(12) United States Patent
Neish et al.

(10) Patent No.: US 10,206,976 B2
(45) Date of Patent: Feb. 19, 2019

(54) PROTEIN PARTICLES COMPRISING DISULFIDE CROSSLINKERS AND USES RELATED THERETO

(71) Applicants: Emory University, Atlanta, GA (US); Georgia Tech Research Corporation, Atlanta, GA (US)

(72) Inventors: Andrew S. Neish, Atlanta, GA (US); Julie A. Champion, Atlanta, GA (US)

(73) Assignees: Emory University, Atlanta, GA (US); Georgia Tech Research Corporation, Atlanta, GA (US)

(*) Notice: Subject to any disclaimer, the term of this patent is extended or adjusted under 35 U.S.C. 154(b) by 0 days.

(21) Appl. No.: 15/946,240

(22) Filed: Apr. 5, 2018

(65) Prior Publication Data

US 2018/0296635 A1    Oct. 18, 2018

Related U.S. Application Data

(62) Division of application No. 14/774,764, filed as application No. PCT/US2014/023175 on Mar. 11, 2014, now Pat. No. 9,962,423.

(60) Provisional application No. 61/778,920, filed on Mar. 13, 2013.

(51) Int. Cl.
*A61K 38/16* (2006.01)
*A61K 47/69* (2017.01)
*A61K 47/64* (2017.01)
*A61K 47/54* (2017.01)
*A61K 45/06* (2006.01)
*C12N 9/10* (2006.01)
*C07K 14/255* (2006.01)

(52) U.S. Cl.
CPC ............ *A61K 38/164* (2013.01); *A61K 45/06* (2013.01); *A61K 47/545* (2017.08); *A61K 47/64* (2017.08); *A61K 47/6929* (2017.08); *C07K 14/255* (2013.01); *C12N 9/1088* (2013.01); *C07K 2319/10* (2013.01); *C07K 2319/21* (2013.01); *C07K 2319/23* (2013.01); *C07K 2319/31* (2013.01); *C07K 2319/60* (2013.01); *C12Y 205/01018* (2013.01)

(58) Field of Classification Search
None
See application file for complete search history.

*Primary Examiner* — Lianko G Garyu
(74) *Attorney, Agent, or Firm* — Emory Patent Group

(57) ABSTRACT

This disclosure relates to particles comprising recombinant proteins, pharmaceutical composition comprising the particles, and therapeutic uses related thereto. In certain embodiments, the particles are made by the process of producing recombinant proteins and conjugating the recombinant proteins to form nanoparticles with a linking reagent comprising disulfide bonds. Typically the recombinant protein has a polypeptide of viral, fungal, or bacterial origin such as secreted effector proteins AvrA and YopJ. In certain embodiments, the disclosure relates to treating or preventing autoimmune diseases, cancer, or inflammatory diseases, or conditions such as inflammatory bowel disease (IBD).

9 Claims, 5 Drawing Sheets

Specification includes a Sequence Listing.

PROTEIN PARTICLES COMPRISING DISULFIDE CROSSLINKERS AND USES RELATED THERETO

CROSS REFERENCE TO RELATED APPLICATIONS

This application is a division of U.S. application Ser. No. 14/774,764 filed Sep. 11, 2015, which is the National Stage of International Application No. PCT/US2014/023175 filed Mar. 11, 2014, which claims the benefit of priority to U.S. Provisional Application No. 61/778,920 filed Mar. 13, 2013. The entirety of each of these applications is hereby incorporated by reference for all purposes.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 12090USDIV_ST25.txt. The text file is 46 KB, was created on Apr. 5, 2018, and is being submitted electronically via EFS-Web.

BACKGROUND

Crohn's disease and ulcerative colitis (Inflammatory bowel disease or IBD) are chronic relapsing disorders of the intestinal tract that may also have systemic manifestations. Symptoms can be debilitating and include abdominal pain and bloody diarrhea. These disorders are generally accepted to result from aberrant immune recognition of the normal commensal microbiota, often associated with an underlying genetic predisposition. They typically manifest with acute and chronic inflammation (granulomatous in the case of Crohn's disease), tissue injury, scarring and predisposition to adenocarcinoma. Additionally, the intestine is the site of other inflammatory conditions including celiac disease, enteric infection and others. Current IBD therapy involves inflammatory suppression with local 5-aminosalicylates, systemic corticosteroids and/or immunosuppressants, or use of endogenous biologicals (anti-TNF monoclonal antibodies (Infliximab) and others). These approaches present complications of systemic immunosuppression and other toxicities. Thus, there is a need to identify improved therapeutic approaches for these diseases.

Traditionally, delivery of most IBD therapeutics has been accomplished by local enema, oral ingestion or systemic infusion. For biologics in particular, injection and oral administration are not ideal because they cannot survive serum proteases, the harsh environment of the gastrointestinal tract, or clearance processes in blood and tissue. Encapsulation of drugs into polymeric carriers can mitigate these limitations.

Nanoparticles have been investigated for a variety of gut applications including vaccination, diabetes, and IBD. Wilson et al., report orally delivered thioketal nanoparticles loaded with TNF-alpha-siRNA target inflammation and inhibit gene expression in the intestines. See Nature Materials, 2010, 9(11): 923-928. Specific biological molecules have been immobilized on nanoparticle surfaces to direct uptake. Russell-Jones reports the use of targeting agents to increase uptake and localization of drugs to the intestinal epithelium. See Journal of Drug Targeting, 2004, 12(2):113-123.

Cohen et al. report enhanced cell penetration of acid-degradable particles functionalized with cell-penetrating peptides. See Bioconjugate Chemistry, 2008, 19(4):876-881. Takayama et al. report enhanced intracellular delivery using arginine-rich peptides by the addition of penetration accelerating sequences (Pas). Journal of Controlled Release, 2009, 138(2):128-133.

Bhavane et al. report the triggered release of ciprofloxacin from nanostructured agglomerated vesicles. See Int J Nanomedicine. 2007, 2(3): 407-418.

Lambert et al., report thiol-exchange in DTSSP crosslinked peptides is proportional to cysteine content. See Protein Sci, 2011, 20(10):1682-91.

References cited herein are not an admission of prior art.

SUMMARY

This disclosure relates to particles comprising recombinant proteins, pharmaceutical composition comprising the particles, and therapeutic uses related thereto. In certain embodiments, the particles are made by the process of producing recombinant proteins and conjugating the recombinant proteins to form nanoparticles with a linking reagent comprising disulfide bonds. In certain embodiments, the recombinant protein has a wild-type polypeptide sequence of a viral, fungal, or bacterial origin such as secreted effector proteins AvrA and YopJ. In certain embodiments, the disclosure relates to treating or preventing autoimmune diseases, cancer, or inflammatory diseases or conditions such as inflammatory bowel disease (IBD).

In certain embodiments, the disclosure relates to particles comprising a) recombinant proteins; and b) linking groups comprising disulfide bonds, wherein the linking groups conjugate the recombinant proteins to form a particle. In certain embodiments, the particles comprise a diameter of about between 50 and 100 nm or 25 and 200 nm or 10 and 500 nm. In certain embodiments, the recombinant protein comprises a viral or bacterial protein, fragment, or combination thereof, such as a secreted effector protein and a flagellin. In certain embodiments, the secreted effector protein is selected from AvrA, mAvrA(C186A), YopJ, VopA, or AopP. In certain embodiments, the secreted effector protein has greater than 10% sequence identity to SEQ ID NO: 1. In certain embodiments, the recombinant secreted effector protein is a fusion comprising the secreted effector protein and an N-terminal or C-terminal polypeptide or amino acid with a primary amino group (e.g., $-CH_2-NH_2$). The free amino group may be the side chain of a lysine. Within a polypeptide the lysine may be separated from the secreted effector protein sequence by a linker such as a glycine or polyglycine. The N-terminal or C-terminal polypeptide may be a polypeptide of greater than two amino acids comprised of glycine, poly-glycine, proline, poly-proline, lysine, poly-lysine and combinations thereof.

In certain embodiments, the disclosure relates to producing particles disclosed herein by mixing recombinant proteins disclosed herein with a linking agent containing a disulfide that reacts with primary amine groups under conditions to form particles. Typically the linking reagent is 3,3'dithiobis(sulfo succinimidyl propionate)(DTSSP). DTSSP contains two sulfo-N-hydroxysuccinimide esters that react with the primary amines in the side chain of lysines and the protein N-terminus.

In certain embodiments, the crosslinking reagent may be any containing a sulfide bond that reacts with primary amine, such as provided in the following formula:

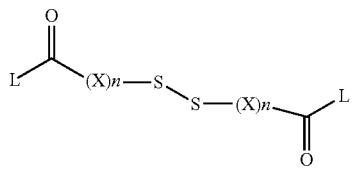

or salts thereof wherein n is 1 to 100, typically n is 1 to 10, or 1 to 6 or 1 to 4, L is a leaving group which reacts with amines to form amides such as an acid anhydride ester, pentafluorophenol ester, thiolester, N-hydoxy heterocyclyl ester, N-hydoxy succinimidyl ester, N-hydroxy sulfosuccinimidyl ester, sulfonic ester, or halogen; and X is at each occurrence individually and independently selected from O, NH, C=O, $CH_2$, $OCH_2$, $CH_2O$, $NHCH_2$, $CH_2NH$, $OCH_2CH_2$, $CH_2CH_2O$, $NHCH_2CH_2$, or $CH_2CH_2NH$. Typically X is $(CH_2)n$ wherein n is 1 to 4.

In certain embodiments, the recombinant protein comprises bovine serum albumin (BSA), green fluorescent protein (GFP), glutathione S-transferase (GST), polyhistidine, polylysine, or combinations thereof. In the case of a fusion protein with a secreted effector protein, the bovine serum albumin (BSA), green fluorescent protein (GFP), glutathione S-transferase (GST), polyhistidine, poly-lysine, or combinations may be on the N-terminal or C-terminal end. In such a case, the opposite end may contain polypeptide or amino acid with a primary amino group (e.g., —$CH_2$—$NH_2$) or it may contain another protein such as a cell penetrating peptide.

In certain embodiments, the recombinant protein is a fusion comprising a protein of interest, e.g., secreted effector protein, and polypeptide or amino acid with a primary amino group (e.g., —$CH_2$—$NH_2$) on the N-terminal and/or C-terminal end and a cell penetrating peptide on the opposite end, e.g., the polypeptide or amino acid with a primary amino group (e.g., —$CH_2$—$NH_2$) is on the C-terminal end, and the cell penetrating peptide is on the N-terminal end. In any of these configurations, arbitrary linking polypeptides or amino acids may be inserted between the protein of interest/ secreted effector protein and the cell penetrating peptide, or linking polypeptides amino acids may be inserted between the protein of interest/secreted effector protein and the polypeptide or amino acid with a primary amino group (e.g., —$CH_2$—$NH_2$). Contemplated linking polypeptides or amino acids may be, but are not limited to, glycine, polyglycine, proline, poly-proline, or combinations thereof. These recombinant fusion proteins optionally contain a targeting polypeptide. Typically the targeting peptides are configured to be exposed on the surface of a particle formed by crosslinking methods disclosed herein, e.g., on the opposite end compared to the polypeptide or amino acid with a primary amino group (e.g., —$CH_2$—$NH_2$) as the purpose of the primary amino group is to allow for crosslinking.

In certain embodiments, it is contemplated that particles herein may be formed from two or more recombinant proteins. For example, a first recombinant protein contains a protein of interest/secreted effector protein and polypeptide or amino acid with a primary amino group, and a second recombinant protein contains a cell penetrating peptide and polypeptide or amino acid with a primary amino group. Particles are formed by mixing the first and second recombinant proteins with a crosslinking reagent that reacts with the primary amino acid groups on both recombinant proteins under conditions to form particles comprising the protein of interest/secreted effector protein and the cell penetrating peptide. In certain embodiments, a third recombinant protein contains a targeting peptide and polypeptide or amino acid with a primary amino group, and particles are formed by mixing first, second, and third recombinant proteins with the crosslinking reagent under conditions such that the desired particles are formed.

In certain embodiments, it is contemplated that additional polypeptide or amino acid with a primary amino group are not included in the recombinant protein, e.g., in the situation where there are sufficient lysine residues at appropriate locations within the wild-type sequence to form the particles by the methods disclosed herein.

In certain embodiments, recombinant proteins disclosed herein comprise a cell penetrating peptide. In certain embodiments, the cell penetrating peptide is oligoarginine peptide (7-12), octa-arginine ($R_8$), the peptide segment (SEQ ID NO: 7) FFLIPKG a penetration accelerating sequence (Pas), Pas-octa-arginine (SEQ ID NO: 8) (FFLIPKG-RRRRRRRR), segment (SEQ ID NO: 9) (GK-PILFF) of cathepsin D-cleavable sequence, segment ($R_8$-cathD, (SEQ ID NO: 10) RRRRRRRR-GKPILFF), or TAT peptide of HIV-1.

In certain embodiments, recombinant proteins and particles disclosed herein comprise a polypeptide with affinity for a cell surface receptor, i.e., targeting polypeptide. In certain embodiments, the targeting polypeptide is a transferrin, EGFR antibody, HER-2 antibody, or ICAM-1 antibody or appropriately binding segments thereof.

In certain embodiments, the disclosure relates to nucleic acids encoding recombinant proteins disclosed herein. In certain embodiments, the disclosure relates to vectors comprising nucleic acids encoding recombinant proteins disclosed herein. In certain embodiments, the disclosure relates expression systems producing recombinant proteins disclosed herein by mixing with vectors comprising nucleic acids encoding recombinant proteins disclosed herein.

In certain, embodiments, the disclosure relates to pharmaceutical compositions comprising particles disclosed herein and a pharmaceutically acceptable excipient, e.g., in the form of a pill, tablet, capsule, or aqueous phosphate buffer solution.

In certain embodiments, the disclosure contemplates methods of treating or preventing a disease or condition disclosed herein comprising administering an effective amount of a pharmaceutical composition comprising particles disclosed herein to a subject in need thereof.

In certain embodiments, the disclosure contemplates methods of treating or preventing inflammatory bowel disease, Crohn's disease, ulcerative colitis, proctitis, fulminant colitis, proctosigmoiditis, left-sided colitis celiac disease, or enteric infection. In certain embodiments, the subject is in need of treatment as the subject is at risk of, exhibiting symptoms, or diagnosed with an inflammatory bowel disease. In certain embodiments, the subject is exhibiting symptoms of abdominal pain or bloody diarrhea or combination thereof. In certain embodiments, the composition is administered in combination with second anti-inflammatory agent such as 5-aminosalicylic acid, sulfasalazine, balsalazide, olsalazine, non-steroidal anti-inflammatory drugs (NSAIDs), aspirin, ibuprofen, cortisone, prednisone, hydrocortisone, methylprednisolone, budesonide, immunosuppressants, mercaptopurine, methotrexate, azathioprine, anti- TNF monoclonal antibodies, infliximab, adalimumab, certolizumab pegol, and golimumab, and etanercept.

In certain embodiment, the disclosure contemplates methods of preparing particles disclosed herein comprising mixing recombinant proteins disclosed herein with crosslinking agents disclosed herein under conditions that particles disclosed herein are formed

BRIEF DESCRIPTION OF THE DRAWINGS

FIG. 1 illustrates schematic of a proposed AvrA nanoparticle therapy for IBD.

FIG. 2 shows Zetasizer data (A, peak 108 nm) and scanning electron micrograph (B, scale bar 300 nm) of AvrA/BSA nanoparticles. Percent fluorescence loss of soluble GFP (dark gray) or nanoparticle GFP (light gray) after 2 hours in intestinal simulation fluid with pancreatin compared to simulation fluid without pancreatin (C).

DETAILED DISCUSSION

Figure 3:
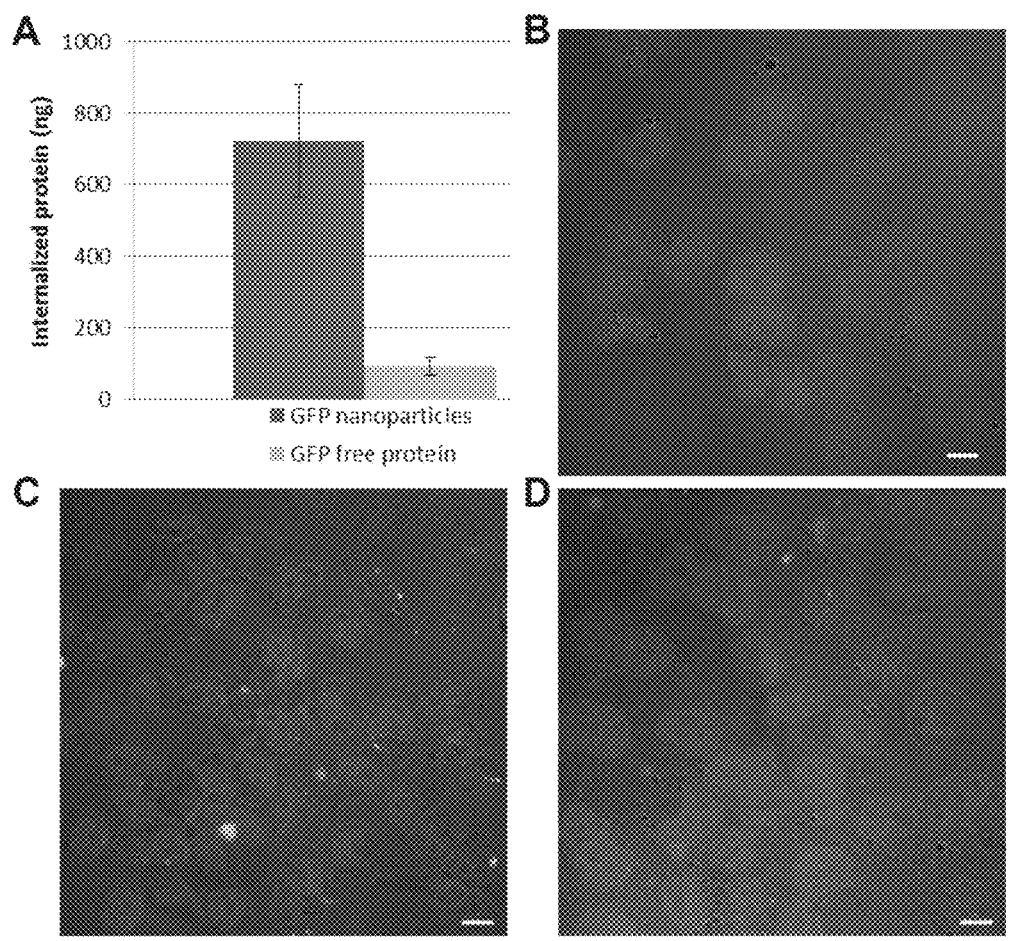
FIG. 3 shows data for recombinant nanoparticles with GFP delivered to HeLa cells (A) soluble protein (light gray) or GFP nanoparticles (dark gray). Confocal images of HeLa cells incubated with GFP nanoparticles for 1 (B), 3 (C), and 6 (D) hours. Images are overlays of GFP fluorescence, nuclear Hoechst dye, and bright field from a slice in the center of cells (scale bar 10 µm).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

"Subject" refers any animal, preferably a human patient, livestock, rodent, monkey or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

The term "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. In contrast, a "regulatable" or "inducible" promoter is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene.

Efficient expression of recombinant nucleic acid sequences in eukaryotic cells requires expression of signals directing the efficient termination and polyadenylation of the resulting transcript. Transcription termination signals are generally found downstream of the polyadenylation signal and are typically a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene.

Sequence "identity" refers to the number of exactly matching residues (expressed as a percentage) in a sequence alignment between two sequences of the alignment. As used herein, percentage identity of an alignment is calculated using the number of identical positions divided by the greater of the shortest sequence or the number of equivalent positions excluding overhangs wherein internal gaps are counted as an equivalent position. For example the polypeptides (SEQ ID NO: 32) GGGGGG and (SEQ ID NO: 33) GGGGT have a sequence identity of 4 out of 5 or 80%. For example, the polypeptides (SEQ ID NO: 34) GGGPPP and (SEQ ID NO: 35) GGGAPPP have a sequence identity of 6 out of 7 or 85%.

Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic-A V I L; Charged positive: R K H; Charged negative—D E; Polar—S T N Q.

The terms "variant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Certain variants have less than 10%, and preferably less than 5%, and still more preferably less than 2% changes (whether substitutions, deletions, and so on).

Role of Commensal and Pathogenic Bacteria in Regulation of Host Inflammatory Pathways The gut exerts defense mechanisms that are tailored to efficiently counter microbial challenges. However, microbes, both pathogens and commensals, have in turn evolved highly effective mechanisms to undermine or modulate the immune system through active manipulation of regulators of the inflammatory response. Enteric pathogens influence eukaryotic cell pathways through soluble effector proteins translocated into the target cells via a "type III secretion apparatus" that usurp host cellular functions for the benefit of the invading organism.

AvrA, is a *Salmonella* protein that is translocated into host cells during initial epithelial cellular invasion. Significantly, homologs of this protein are found in a variety of bacteria, both pathogens and symbionts, which are intimately associated with animal and plant eukaryotic hosts. The protein family members are acetyltransferases that covalently modify and inactivate members of the MAPK superfamily, and thus have potent and diverse effects on a wide variety of eukaryotic growth, survival and immune pathways. AvrA overexpressed in transfected cells or in a *Drosophila* transgenic model blocks activation of NF-κB, MAPK, JNK, and transcriptional activation of a range of inflammatory effector genes. In yeast, flies, human cells and murine intestinal epithelia, immune blockade occurs without induction of the apoptotic cell death characteristically seen during inhibition of host stress signaling pathways. The biochemical profile of JNK/NF-κB suppression combined with ERK activation results in inflammatory suppression without stimulating apoptosis or other types of cellular death.

Secreted Effector Proteins of Pathogens

In certain embodiments, the disclosure relates to nanoparticles comprising recombinant proteins wherein the recombinant protein comprises a viral, fungal, or bacterial protein sequence such as a secreted effector protein selected from AvrA, mAvrA(C186A), YopJ, VopA, or AopP.

Experiments disclosed herein utilize a secreted *Salmonella* protein with homology to avirulence determinants of plant pathogenic bacteria (AvrA *Salmonella enterica*)—see Hardt & Galan, PNSA, 1997, 94 (18):9887-9892—having the following amino acid sequence, (SEQ ID NO: 1) MIFSVQELSC GGKSMLSPTT RNMGASLSPQ PDVS-GELNTE ALTCIVERLE SEIIDGSWIH ISYEETDLEM MPFLVAQANK KYPELNLKFV MSVHELVSSI KET-RMEGVES ARFLVNMGSS GIHISVVDFR VMDGKTS-VIL FEPAACSAFG PALALRTKAA LEREQLPDCY FAMVELDIQR SSSECGIFSL ALAKKLQLEF MNLVKI-HEDN ICERLCGEEP FLPSDKADRY LPVSFYKHTQ GAQRLNEYVE ANPAAGSSIV NKKNETLYER FDN-NAVMLND KKLSISAHKK RIAEYKSLLK P.

AvrA has a YopJ domain, i.e., AvrA sequence is minus amino acids 1-14. Yoon et al., report *Yersinia* effector YopJ inhibits yeast MAPK signaling pathways by an evolutionarily conserved mechanism. See J Biol Chem, 2003, 278 (4):2131-5. *Salmonella enterica* YopJ has the following sequence (SEQ ID NO: 2) MLSPTARNMG ASLSPQPDVS GELNTEALTC IVERLESEII DGSWIHISYE ETDLEMMPFL VAQANKKYPE LNLKFVMSVH ELVSSIKETR MEGVESARFI VNMGSSGIHI SVVD-FRVMDG KTSVILFEPA ACSAFGPALL ALRTKAALER EQLPDCYFAM VELDIQRSSS ECGIFSLALA KKLQLEFMNL VKIHEDNICE RLCGEEPFLP SDKADRYLPV SFYKHTQGVQ RLNEYVQANP AAGSSIVNKK NETLYERFDN NAVMLNDKKL SISAH-KKRIA EYKSLLKP.

In certain embodiments, the term "AvrA" refers to proteins of any bacteria that have substantial homology to SEQ ID NO:1 and variants. In certain embodiments, nanoparticles are comprised of recombinant proteins having greater than 30%, 40%, 50%, 60%, 70%, 80%, 90%, or 95% sequence identity or similarity to SEQ ID NO:1. In certain embodiments, the disclosure contemplates variants that are substitutions, deletions, or insertions of about, less than, or more than, one, two, three, four, five, six, seven, eight, nine, ten, eleven, twelve, thirteen, fourteen, fifteen, or sixteen amino acids. In certain embodiments, the substitutions are conserved substitutions. In certain embodiments, the substitutions, deletions, or insertions are not within the YopJ domain. In certain embodiments, one, two, three, or four substitutions, deletions, or insertions are within the YopJ domain. In certain embodiments, nanoparticles disclosed herein comprise a polypeptide that has greater than 30%, 40%, 50%, 60%, 70%, 80%, 90%, or 95% sequence identity or similarity to SEQ ID NO:2. In certain embodiments, the disclosure contemplates variants that are substitutions, deletions, or insertions of one, two, three, four, five, six, seven, eight, nine, or ten amino acids. In certain embodiments, the substitutions are conserved substitutions.

In certain embodiments, the nanoparticles comprise a polypeptide with a YopJ domain or any member of the YopJ superfamily, i.e., NCBI superfamily c107849 available at http://www.ncbi.nlm.nih.gov/Structure/cdd/cddsrv.cgi?uid=c107849. One example is Vibrio outer protein J (VopJ) of the following sequence (SEQ ID NO: 3) MKVNLEQNHY YEQRGGSDLR EQLSSYIDLM DDAIRQGKQL PKDTAAANDI ALMDDFIAIA NQKKEGLNAH FFRSPLDMVN YVKSLIPSED TTARFVVNMG SGGIHCIAVD CAIKNGKCSL IGIEPVTMNS LGASMLAIRL QSVCKRELPE TSLVIMETDM QRSQGECLMF SLFLVKKMHK ECDEFQYLHD KNINRELPLT QGLIVSVKDA DSLLPPSLMK HTQSPNRLQK YLEMRPEAMN CVVNKKGETL KTRQQRHITT IELGEKTVSY SNSIEQKRIK EAKGLLNNL.

Another contemplated example is Vibrio outer protein A (VopA) comprising the following sequence (SEQ ID NO:4) ndialipdfi diankkkagl naifcnnple mvekvkqlll lenssarfiv nlgcggihcm avdclvsdgk csligiepvg mnssgpalla irlqsickre lpeaalaife tdmqrsygec amfslflvkk mhkesaqfqe lhkknidqnl pksgeiivsv sqtnnllpps lmkhvqspkr leaylesrpe aadvvvnkkg etllsrqqry iatiea.

Another contemplated example is Aeromonas outer protein P (AopP) comprising the following sequence (SEQ ID NO:5) mnippihikt dltnqdektt iqeatkeelq lliatmerel asgefftshe nyasidlgkm pllieaannk hvglnlnfvs npidlpseig raisngkeqf ryvvnmgesg ihfaaidckm vdgklslllm epanlnsmgp amlamrvssc lkreaeiipk phfciavmdi qrsnsecgif svglakkmfs erapldalhe eilserlpdg mkcdvlegea ldrllpptfy khaqsqrrld qyirahpdgn dtsvnkkgel lldrakrlmv pvdeklisss ihqkrimeys aisddgksv.

In certain embodiments, nanoparticles disclosed herein comprise a polypeptide of greater than 30%, 40%, 50%, 60%, 70%, 80%, 90%, or 95% sequence identity or similarity to a YopJ superfamily protein. In certain embodiments, the disclosure contemplates variants that are substitutions, deletions, or insertions of one, two, three, four, five, six, seven, eight, nine, or ten amino acids. In certain embodiments, the substitutions are conserved substitutions.

Cell penetrating peptides (CCPs)

In certain embodiments, the disclosure relates to particles comprising recombinant proteins which are a chimeric or fusion protein comprising a cell penetrating peptide (CCP) in combination with a bacteria secreted effector protein. CPPs typically have an amino acid composition that either contains a high relative abundance of positively charged amino acids such as lysine or arginine or has sequences that contain an alternating pattern of polar/charged amino acids and non-polar, hydrophobic amino acids referred to as polycationic or amphipathic, respectively.

In one example, the CPP is trans-activating transcriptional activator (Tat) from Human Immunodeficiency Virus 1 (HIV-1) (SEQ ID NO:6) MEPVDPRLEP WKHPGSQPKT PCTKCYCKKC CLHCQVCFMT KGLGISYGRK KRRQRRRAPQ DNKNHQVSLS KQPTSRARGD PTGQEESKEK VEKETVVDPV T and variants thereof. In certain embodiments, nanoparticles disclosed herein comprise a polypeptide of greater than 70%, 80%, 90%, or 95% sequence identity or similarity to TAT peptide of HIV-1. In certain embodiments, the disclosure contemplates variants that are substitutions, deletions, or insertions of one, two, three, four, five, six, seven, eight, nine, or ten amino acids. In certain embodiments, the substitutions are conserved substitutions.

Additional examples of contemplated CCPs are selected from oligoarginine peptide (7-12), octa-arginine ($R_8$), the peptide segment (SEQ ID NO: 7) FFLIPKG a penetration accelerating sequence (Pas), Pas-octa-arginine (SEQ ID NO: 8) FFLIPKG-RRRRRRRR, segment with (SEQ ID NO: 9) GKPILFF of cathepsin D-cleavable sequence, and a segment $R_8$-cathD, (SEQ ID NO: 10) RRRRRRRR-GKPILFF. Additional examples of CPPs are (SEQ ID NO: 11) GALFLGFLGA$_{10}$AGSTMGAWSQ$_{20}$PKKKRKV and GALFLAFLAA$_{10}$ALSLMGLWSQ$_{20}$PKKKRKV (SEQ ID NO: 12) as disclosed in Deshayes et al., Biochemistry, 2004, 43 (24), pp 7698-7706; (SEQ ID NO: 13) RVIRVWFQNKRCKDKK and (SEQ ID NO: 14) RQIKIWFQNRRMKWKK and (SEQ ID NO: 15) GWTLNSAGYLLGKINLKALLAALAKKIL as disclosed in Magzoub et al., Biochim Biophys Acta, 2001, 1512(1):77-89.

In one example, CCP is a transferrin (Tf). The wild-type human Tf is a 679 amino acid protein of approximately 75 kDa (not accounting for glycosylation), with two main domains or lobes, N (about 330 amino acids) and C (about 340 amino acids). See GenBank accession numbers NM_001063, XM_002793, M12530, XM_039845, XM_039847 and 595936, all of which are herein incorporated by reference in their entirety, as well as SEQ ID NO: 16 (SEQ ID NO: 16 comprises the additional 19 amino acid sequence of the human transferrin leader sequence).

```
MRLAVGALLV CAVLGLCLAV PDKTVRWCAV SEHEATKCQS

FRDHMKSVIP SDGPSVACVK KASYLDCIRA IAANEADAVT

LDAGLVYDAY LAPNNLKPVV AEFYGSKEDP QTFYYAVAVV

KKDSGFQMNQ LRGKKSCHTG LGRSAGWNIP IGLLYCDLPE

PRKPLEKAVA NFFSGSCAPC ADGTDFPQLC QLCPGCGCST

LNQYFGYSGA FKCLKDGAGD VAFVKHSTIF ENLANKADRD

QYELLCLDNT RKPVDEYKDC HLAQVPSHTV VARSMGGKED

LIWELLNQAQ EHFGKDKSKE FQLFSSPHGK DLLFKDSAHG

FLKVPPRMDA KMYLGYEYVT AIRNLREGTC PEAPTDECKP

VKWCALSHHE RLKCDEWSVN SVGKIECVSA ETTEDCIAKI

MNGEADAMSL DGGFVYIAGK CGLVPVLAEN YNKSDNCEDT
```

```
PEAGYFAVAV VKKSASDLTW DNLKGKKSCH TAVGRTAGWN

IPMGLLYNKI NHCRFDEFFS EGCAPGSKKD SSLCKLCMGS

GLNLCEPNNK EGYYGYTGAF RCLVEKGDVA FVKHQTVPQN

TGGKNPDPWA KNLNEKDYEL LCLDGTRKPV EEYANCHLAR

APNHAVVTRK DKEACVHKIL RQQQHLFGSN VTDCSGNFCL

FRSETKDLLFRDDTVCLAKLHDRNTYEKYL GEEYVKAVGN

LRKCSTSSLL EACTFRRP
```

Recombinant proteins disclosed herein may be made with any Tf protein, fragment, domain, or engineered domain. For instance, recombinant proteins may be produced using the full-length Tf sequence, with or without the native Tf signal sequence. Tf recombinant proteins may also be made using a single Tf domain, such as an individual N or C domain or a modified form of Tf comprising 2N or 2C domains (see U.S. Pat. Appl. Publ. No. US 2006/0130158).

Other contemplated transferrin variants are provided in U.S. Pat. No. 8,158,579 (modified Tf). In certain embodiments, this disclosure contemplates particles comprising recombinant proteins disclosed herein comprising a transferrin variant of the following sequence (SEQ ID NO: 17)

Val Pro Asp Lys Thr Val Arg Trp Cys Ala Val Ser Glu

His Glu Ala Thr Lys Cys Gln Ser Phe Arg Asp His Met Lys Ser Val

Ile Pro Ser Asp Gly Pro Ser Val Ala Cys Val Lys Lys Ala Ser Tyr

Leu Asp Cys Ile Arg Ala Ile Ala Ala Asn Glu Ala Asp Ala Val Thr

Leu Asp Ala Gly Leu Val Tyr Asp Ala Tyr Leu Ala Pro Asn Asn Leu

Lys Pro Val Val Ala Glu Phe Tyr Gly Ser Lys Glu Asp Pro Gln Thr

Phe Tyr Tyr Ala Val Ala Val Val Lys Lys Asp Ser Gly Phe Gln Met

Asn Gln Leu Arg Gly Lys Lys Ser Cys His Thr Gly Leu Gly Arg Ser

Ala Gly Trp Asn Ile Pro Ile Gly Leu Leu Tyr Cys Asp Leu Pro Glu

Pro Arg Lys Pro Leu Glu Lys Ala Val Ala Asn Phe Phe Ser Gly Ser

Cys Ala Pro Cys Ala Asp Gly Thr Asp Phe Pro Gln Leu Cys Gln Leu

Cys Pro Gly Cys Gly Cys Ser Thr Leu Asn Gln Tyr Phe Gly Tyr Ser

Gly Ala Phe Lys Cys Leu Lys Asp Gly Ala Gly Asp Val Ala Phe Val

Lys His Ser Thr Ile Phe Glu Asn Leu Ala Asn Lys Ala Asp Arg Asp

Gln Tyr Glu Leu Leu Cys Leu Asp Asn Thr Arg Lys Pro Val Asp Glu

Tyr Lys Asp Cys His Leu Ala Gln Val Pro Ser His Thr Val Val Ala

Arg Ser Met Gly Gly Lys Glu Asp Leu Ile Trp Glu Leu Leu Asn Gln

Ala Gln Glu His Phe Gly Lys Asp Lys Ser Lys Glu Phe Gln Leu Phe

Ser Ser Pro His Gly Lys Asp Leu Leu Phe Lys Asp Ser Ala His Gly

Phe Leu Lys Val Pro Pro Arg Met Asp Ala Lys Met Tyr Leu Gly Tyr

Glu Tyr Val Thr Ala Ile Arg Asn Leu Arg Glu Gly Thr Cys Pro Glu

Ala Pro Thr Asp Glu Cys Lys Pro Val Lys Trp Cys Ala Leu Ser His

His Glu Arg Leu Lys Cys Asp Glu Trp Ser Val Asn Ser Val Gly Lys

Ile Glu Cys Val Ser Ala Glu Thr Thr Glu Asp Cys Ile Ala Lys Ile

Met Asn Gly Glu Ala Asp Ala Met Ser Leu Asp Gly Gly Phe Val Tyr

Ile Ala Gly Lys Cys Gly Leu Val Pro Val Leu Ala Glu Asn Tyr Asn

Lys Ala Asp Asn Cys Glu Asp Thr Pro Glu Ala Gly Tyr Phe Ala Val

Ala Val Val Lys Lys Ser Ala Ser Asp Leu Thr Trp Asp Asn Leu Lys

Gly Lys Lys Ser Cys His Thr Ala Val Gly Arg Thr Ala Gly Trp Asn

Ile Pro Met Gly Leu Leu Tyr Asn Lys Ile Asn His Cys Arg Phe Asp

Glu Phe Phe Ser Glu Gly Cys Ala Pro Gly Ser Lys Lys Asp Ser Ser

Leu Cys Lys Leu Cys Met Gly Ser Gly Leu Asn Leu Cys Glu Pro Asn

Asn Lys Glu Gly Tyr Tyr Gly Tyr Thr Gly Ala Phe Arg Cys Leu Val

Glu Lys Gly Asp Val Ala Phe Val Lys His Gln Thr Val Pro Gln Asn

Thr Gly Gly Lys Asn Pro Asp Pro Trp Ala Lys Asn Leu Asn Glu Lys

Asp Tyr Glu Leu Leu Cys Leu Asp Gly Thr Arg Lys Pro Val Glu Glu

Tyr Ala Asn Cys His Leu Ala Arg Ala Pro Asn His Ala Val Val Thr

Arg Lys Asp Lys Glu Ala Cys Val His Lys Ile Leu Arg Gln Gln Gln

His Leu Phe Gly Ser Asn Val Ala Asp Cys Ser Gly Asn Phe Cys Leu

Phe Arg Ser Glu Thr Lys Asp Leu Leu Phe Arg Asp Asp Thr Val Cys

Leu Ala Lys Leu His Asp Arg Asn Thr Tyr Glu Lys Tyr Leu Gly Glu

Glu Tyr Val Lys Ala Val Gly Asn Leu Arg Lys Cys Ser Thr Ser Ser

Leu Leu Glu Ala Cys Thr Pro Arg Arg Pro or variants thereof.

In certain embodiments, nanoparticles disclosed herein comprise a polypeptide of greater than 30%, 40%, 50%, 60%, 70%, 80%, 90%, or 95% sequence identity or similarity to SEQ ID NOs: 16 or 17.

Engineered Nanoparticle Components for Intracellular Delivery

Traditionally, delivery of most IBD therapeutics has been accomplished by local enema, oral ingestion or systemic infusion. For biologics in particular, injection and oral administration are not ideal because they cannot survive serum proteases, the harsh environment of the gastrointestinal tract, or clearance processes in blood and tissue. Encapsulation of drugs into polymeric carriers can mitigate these limitations. Prior to release, the polymer protects drugs from degradation or premature metabolism and particles can deliver a concentrated dose of drug. Targeting ligands can also be attached to the particle surface to direct accumulation of particles at a particular site, thereby increasing the drug concentration locally while minimizing systemic side effects. These benefits have typically been realized by particles carrying small molecule drugs. In the case of protein drugs, however, this delivery strategy still has limitations. Protein loading is extremely low, the particles are often too large to be internalized by cells (≥50 μm), and harsh fabrication or degradation conditions can damage the protein. Hydrophilic polymers, biopolymers, or albumin may be used as the encapsulating material.

Figures 1, 2:
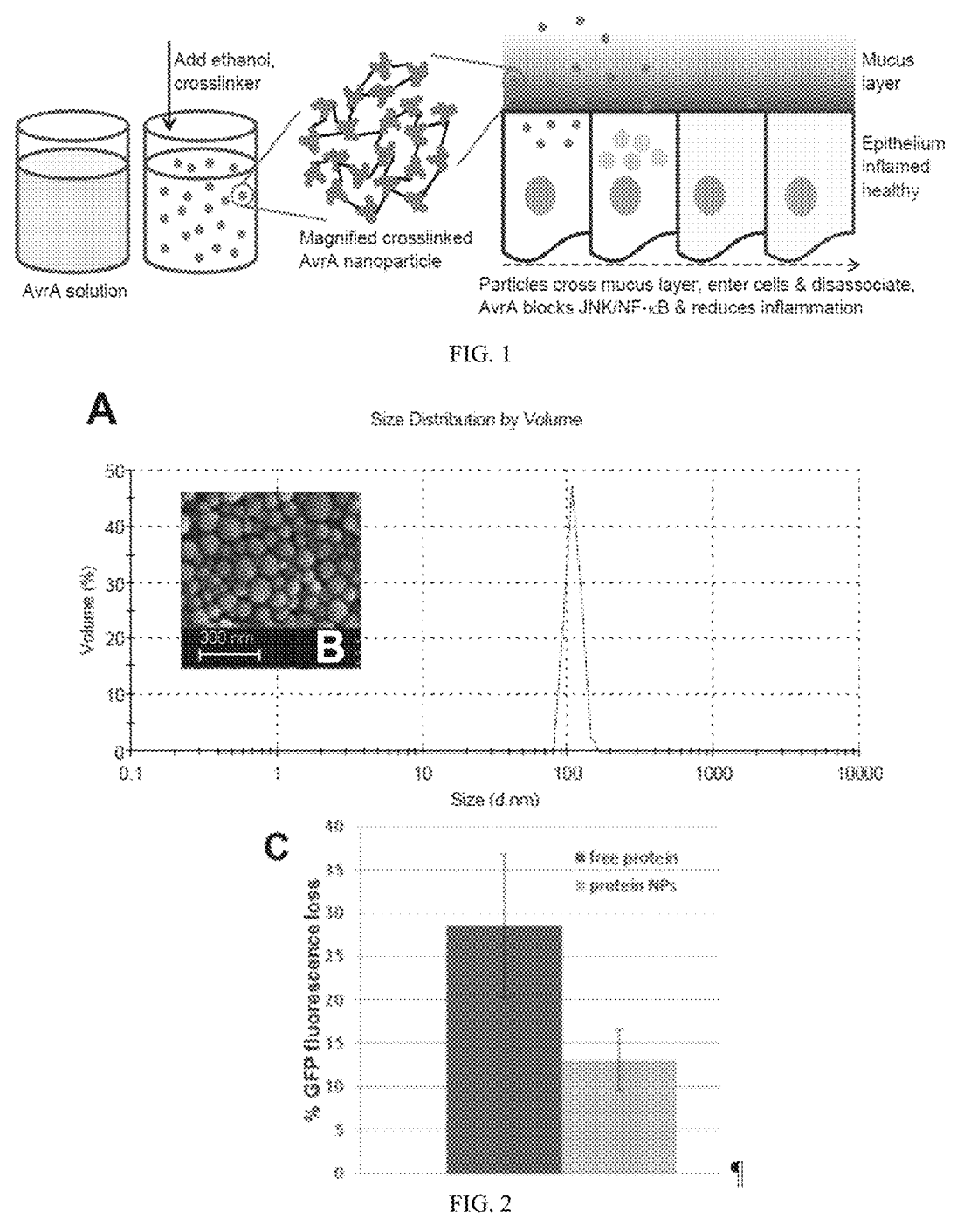
Figure 7:
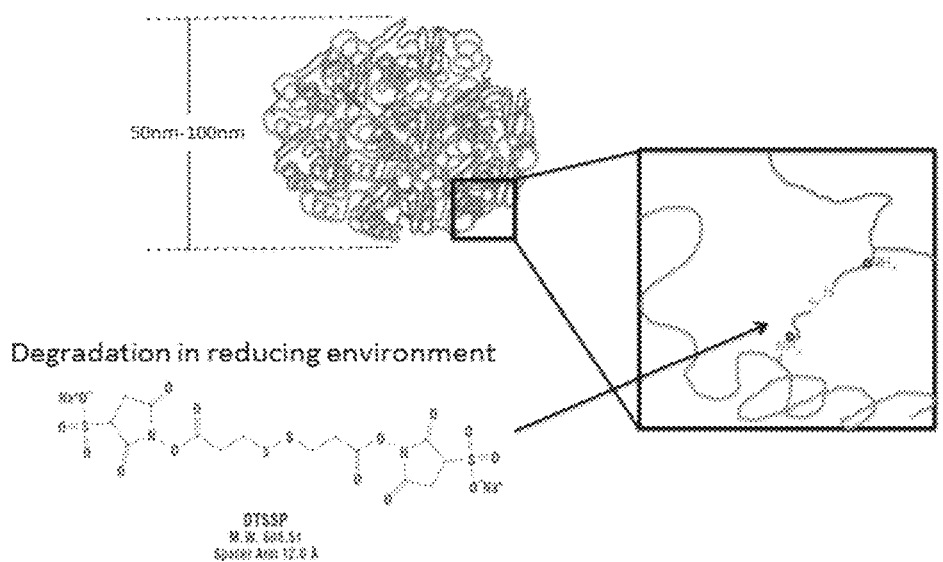
FIG. 7 illustrates crosslinking of recombinant proteins.
Figure 8:
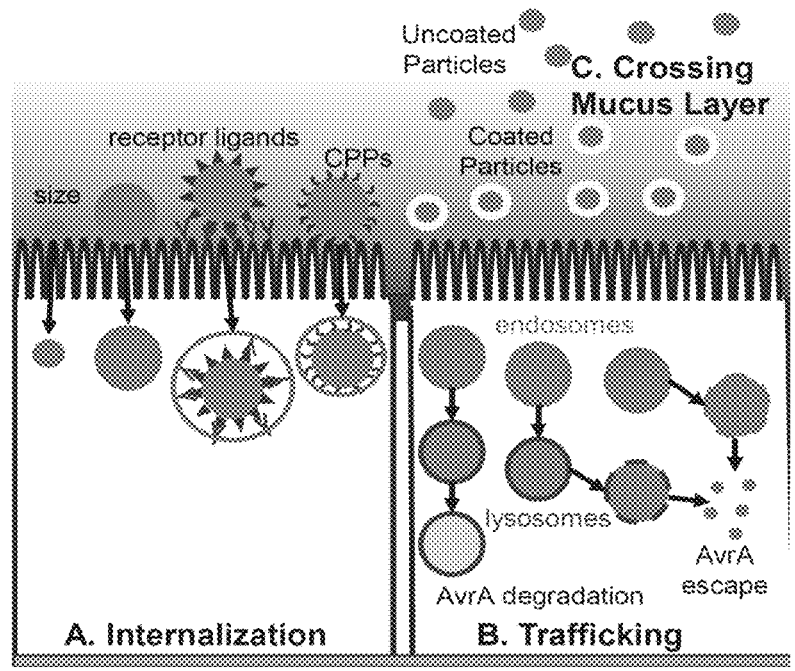
FIG. 8 illustrates nanoparticle delivery barriers. (A) Internalization controlled via particle size, receptor ligands and cell penetrating peptides (CPPs). (B) Particle escape from endo/lysosomes and disassembly will be controlled via endolytic peptides and crosslinking density. (C) Hydrophilic coatings aid particle transport across mucus layer.
Figure 9:
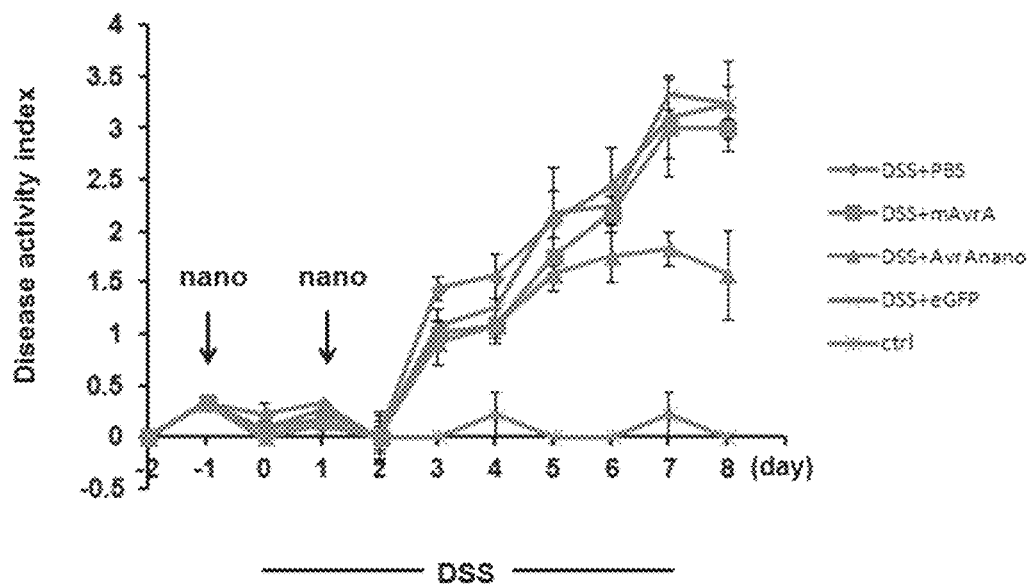
FIG. 9 shows data indicating a therapeutic effect of AvrA nanopartilces in a colitis model. Nanoparticles, including active (AvrAnano), mutant inactive (mAvrA) and inert control (eGFP) were administered transrectally at two indicated time points to groups of 5 mice. Phosphate buffered saline (PBS) was administered as a negative control. Model colitis was induced by the addition of dextran sodium sulfate in drinking water at day 0 to day 7. No treatments were given to control (ctrl) mice. All animals were followed daily and weight, presence of fecal blood, and diarrhea were used to derive a disease activity index (DAI).

Contemplated embodiments nanoparticles of this disclosure are illustrated are illustrated in FIGS. 1, 7, and 8. Nanoparticle surface chemistry is important in dictating initial interactions with mucus and the cell membrane, as well as subsequent internalization routes (FIGS. 8A,C). Surface chemistry can refer to the general surface charge or hydrophobicity of a particle. For the nanoparticles disclosed herein, these two features are a function of the core material, AvrA. One of the benefits of nanoparticle delivery systems is the ability to modify particle surfaces independently of the cargo. Within certain embodiments of the disclosure nanoparticles targeting cell surface receptors and utilizing cell penetrating peptides (CPPs) inspired by viral pathogens are contemplated. In one embodiment, the transferrin receptor is attached to the surface of nanoparticles with the same crosslinking strategy used to form AvrA nanoparticles. CPPs are short peptide sequences that enhance intracellular internalization. In certain embodiments, the CPP, octa-arginine, modeled on the TAT peptide used by HIV-142, is inserted into the AvrA DNA sequence and incorporated during in vivo recombinant protein expression. CPPs significantly increase endocytic uptake.

Nanoparticles are taken up into endocytic pathway. AvrA reaches cytosol in order to achieve bioactivity (FIG. 8B). In certain embodiments, particles disclosed herein comprise a protein with the following sequence (SEQ ID NO: 18) WG(Pal)VKIKKP9GGH6 wherein Pal is a palmitoyl group anchored to a synthetic diaminopropionic acid (Dap) residue. This is an amphiphilic palmitoylated peptide which promotes endosomal escape. See Delehanty et al., Integrative Biology, 2010, 2(5-6):265-277. These peptides may be synthesized on solid supports and either physically adsorbed on the nanoparticle surface (due to their amphiphilic nature) or covalently bound. If covalent chemistry is necessary the carboxyl terminus of peptides may be activated by the carbodiimide EDC and then linked to free amines on the particle surface.

In certain embodiments, particles disclosed herein comprise a recombinant protein with greater than 20 amino acids of N-terminal sequence of the influenza virus hemagglutinin subunit HA-2. Peptides derived from influenza hemagglutinin are capable of inducing lysis of the endosome. See Wagner et al., PNSA, 1992, 89(17):7934-7938. For example, in certain embodiments, the disclosure contemplates recombinant proteins with the amino acid sequences (SEQ ID NO: 19) Gly-Leu-Phe-Glu-Ala-Ile-Ala-Gly-Phe-Ile-Glu-Asn-Gly-Trp-Glu-Gly-Met-Ile-Asp-Gly-Gly-Gly-Cys and (SEQ ID NO: 31) Phe-Leu-Gly-Ile-Ala-Glu-Ala-Ile-Asp-Ile-Gly-Asn-Gly-Trp-Glu-Gly-Met-Glu-Phe-Gly-Gly-Gly-Cys optionally in combination with a polylysine made by the process of inserting them in the AvrA DNA sequence for subsequent protein translation.

Nanoparticle design incorporates a variety of factors including size, surface chemistry, endosomal escape mechanisms, and crosslinking type and density. Each feature has the capability to influence internalization and trafficking processes shown in FIG. 8. Additionally, they can also impact nanoparticle interactions with mucus and general stability in vivo. In certain embodiment, the disclosure contemplates particles of a size typically of less than 200 nm in diameter and greater than 50 nm in diameter. In certain embodiments the disclosure contemplates providing a hydrophilic or neutral coating such as polyethylene glycol. The polymer PEG may be adsorb on the particle surface or a covalent approach may be used.

Enhanced targeting to injured tissue may be achieved by altering the particle binding specificity. For example, intracellular adhesion molecule 1 (ICAM-1) is upregulated on intestinal epithelial cells in areas of inflammation and after exposure to invasive bacteria. In certain embodiments, the disclosure contemplates recombinant protein particles disclosed herein with anti-ICAM-1 antibodies, e.g., conjugated or adsorbed to the surface as with PEG. While targeting strategies or inherent mucus differences can bias nanoparticles toward inflamed tissue, there may be advantages to nanoparticles interacting with healthy epithelium as well. This could be useful for protective treatments prior to injury/colitis induction. Additional targeting agents include EGFR and HER-2 antibodies such as cetuximab, erlotinib, and gefitinib particularly for uses in the treatment of breast or prostate cancer.

In certain embodiments, the disclosure contemplates that the particles disclosed herein may comprise an enteric coating. The enteric coating may comprise traditional polymeric coating such as methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, sodium alginate, and stearic acid. The nanoparticles can be encapsulated into microparticles of a chitosan and/or alginate composition by forming an emulsion and calcium crosslinking.

While a specific *Salmonella* protein, AvrA, has been chosen as a model immunesuppressive protein for packing into nanoparticles for IBD therapy, this approach is actually very general. There are a variety of bacterial proteins that have been shown to suppress or enhance immune signaling and likely more that have not yet been discovered or characterized. For example, AvrA family members (YopJ, VopA, AopP) that have variable effects on MAPK and are more potently immunesuppressive, but also pro-apoptotic. Other candidate immune-modulatory effectors include OspG/F from *Shigella* that inhibit the ubiquitination step of NF-κB.

Flagellin

Also contemplated by this disclosure is the use of TLR ligands such as flagellin, peptidioglycans, and other immunostimulatory molecules. Packaged TLR ligands could serve as immunostimulatory vaccine adjuvants or cytoprotective molecules. These ligands are also amenable for nanoparticle fabrication.

As used herein, "a flagellin" refers to the monomer subunit in flagella, e.g., flagellin gene product of FliC and FljB in *S. typhimurium* and FlaA in *L. pneumophila*, or variants, homologs, derivatives, fragments or combination thereof, such as a domain or polypeptide sequence in the domain. Typically, the flagellin monomer contains D0, D1, D2, and D3 domains. An alignment of the amino acid sequences from different Gram-negative species shows a high degree of similarity in the amino and carboxy terminal domains. The central regions of these proteins may be quite divergent. It is believed that flagellin responsible for interaction with TLR5 is found in the D1 domain. Smith, K. D., et al, Nature Immunol. (2003) 4:1247-1253 disclose that TLR5 recognizes a site on the flagellin of *Salmonella typhimurium* (FliC) composed of N-terminal residues 78-129 and 135-173 and C-terminal residues 395-444. The term "a flagellin" is not intended to be limited to any particular amino acid sequence provided that it has some homology to known flagellin sequences and the molecule retains the ability to stimulate innate immune responses. The innate immune responses of flagellin are known to includes cytokine production in response to TLR (including TLR5) activation and activation of Caspase-1 and IL-1β secretion in response to certain NLRs (including Ipaf). In certain embodiments, a flagellin is contemplated to include additional amino acids within the sequence, such as in the case of fusion or chimeric proteins, provided that these proteins continue to affect an innate immune response that comprises a TLR5-mediated immune response, an Ipaf-mediated immune response or both. Also specifically contemplated are fragments, variants, analogs, homologs, or derivatives of said flagellin, and combinations thereof provided these molecules continue to affect an innate immune response that comprises a TLR5-mediated immune response, an Ipaf-mediated immune response or both. A flagellin may be isolated from natural sources, by synthetic or recombinant technologies or combinations thereof.

Individual *salmonella* serotypes usually alternate between the production of two forms of flagellin, termed phase 1 and phase 2, each specified by separate structural genes FliC and FljB. The amino acid sequences of phase-1 flagella protein of *salmonella typhimurium* (FliC) is set forth in SEQ ID NO: 20 MAQVINTNSL SLLTQNNLNK SQSALGTAIE RLSSGLRINS AKDDAAGQAI ANRFTANIKG LTQASRNAND GISIAQTTEG ALNEINNNLQ RVRELAVQSA NSTNSQSDLD SIQAEITQRL NEIDRVSGQT QFNGVKVLAQ DNTLTIQVGA NDGETIDIDL KQINSQTLGL DTLNVQQKYK VSDTAATVTG YADTTIALDN STFKASATGL GGTDQKIDGD LKFDDTTGKY YAKVTVTGGT GKDGYYEVSV DKTNGEVTLA GGATSPLTGG LPATATEDVK NVQVANADLT EAKAALTAAG VTGTASVVKM SYTDNNGKTI DGGLAVKVGD DYYSATQNKD GSISINTTKY TADDGTSKTA LNKLGGADGK TEVVSIGGKT YAASKAEGHN FKAQPDLAEA AATTTENPLQ KIDAALAQVD TLRSDLGAVQ NRFNSAITNL GNTVNNLTSA RSRIEDSDYA TEVSNMSRAQ ILQQAGTSVL AQANQVPQNV LSLLR.

In certain embodiments, nanoparticles disclosed herein comprise a polypeptide of greater than 30%, 40%, 50%, 60%, 70%, 80%, 90%, or 95% sequence identity or similarity to SEQ ID NO: 20.

The amino acid sequences of F41 fragment of flagellin of *salmonella typhimurium* is set forth in SEQ ID NO: 21, FTANIKGLTQ ASRNANDGIS IAQTTEGALN EINNNLQRVR ELAVQSANST NSQSDLDSIQ AEITQRLNEI DRVSGQTQFN GVKVLAQDNT LTIQVGANDG ETIDIDLKQI NSQTLGLDTL NVQQKYKVSD TAATVTGYAD TTIALDNSTF KASATGLGGT DQKIDGDLKF DDTTGKYYAK VTVTGGTGKD GYYEVSVDKT NGEVTLAGGA TSPLTGGLPA TATEDVKNVQ VANADLTEAK AALTAAGVTG TASVVKMSYT DNNGKTIDGG LAVKVGDDYY SATQNKDGSI SINTTKYTAD DGTSKTALNK LGGADGKTEV VSIGGKTYAA SKAEGHNFKA QPDLAEAAAT TTENPLQKID AALAQVDTLR SDLAAVQNRF NSAITNLGNT VNNLTSAR.

The amino acid sequences of a flagellin fusion protein is set forth in SEQ ID NO:22, MALTVNTNIA SLNTQRNLNN SSASLNTSLQ RLSTGSRINS AKDDAAGLQI ANRLTSQVNG LNVATKNAND GISLAQTAEG ALQQSTNILQ RMRDLSLQSA NGSNSDSERT ALNGEVKQLQ KELDRISNTT TFGGRKLLDG SFGVASFQVG SAANEIISVG IGGGKLMIKL KFGVFFTVLL SSAYAHGTPQ NITDLCAEYH NTQIHTLNDK IFSYTE SLAG KREMAIITFK NGATFQVEVP GSQHIDSQKK AIERMKDTLR IAYLTEAKVE KLCVWNNKTP HAIAAISMAN.

Polypeptide fragments of flagellin include SEQ ID NO: 23, GALNEINNNL QRVRELAVQ SANSTNSQS DLDSIQAE ITQ;

SEQ ID NO: 24, TQFSGVKVLAQDNTLTIQVGANDGET IDIDLKQINS QTLGLDTL;

SEQ ID NO: 25, EGALNEINN NLQRVRELA VQSANSTNS QSDLDSIQAEITQRLNEIDRVNG;

SEQ ID NO: 26, MAQVINTNSL SLLTQNNLNK SQSALGTAI ERLSSGLRINSAKD DAAGQAIANF TANIKGLTQA SRNANDGISI AQTTEGALN EINNNLQRVRELAVQS;

SEQ ID NO: 27, LQKIDAALAQVDTLRSDLGAVQNRFNSAITNL;

SEQ ID NO: 28, TLRSDLGAVQNRFNSAITNLGNTVNNLSS; and

SEQ ID NO: 29, EQAAKTTENPLQKIDAALAQVDTLRSDLGAVQNRFNS AITNLGNTVNNLSS.

Combination of fragments of flagellin include SEQ ID NO: 30, Met Arg Gly Ser His His His His His His Gly Met Ala Ser Met Thr1 Gly Gln Gln Met Gly Arg Asp Leu Tyr Asp Asp Asp Asp Lys Asp Pro Met Ala Gln Val Ile Asn Thr Asn Ser Leu Ser Leu Leu Thr Gln Asn Asn Leu Asn Lys Ser Gln Ser Ser Leu Ser Ser Ala Ile Glu Arg Leu Ser Ser Gly Leu Arg Ile Asn Ser Ala Lys Asp Asp Ala Ala Gly Gln Ala Ile Ala Asn Arg Phe Thr Ser Asn Ile Lys Gly Leu Thr Gln Ala Ser Arg Asn Ala Asn Asp Gly Ile Ser Ile Ala Gln Thr Thr Glu Gly Ala Leu Asn Glu Ile Asn Asn Asn Leu Gln Arg Val Arg Glu Leu Ser Val Gln Ala Thr Asn Gly Thr Asn Ser Asp Ser Asp Leu Lys Ser Ile Gln Asp Glu Ile Gln Gln Arg Leu Glu Glu Ile Asp Arg Val Ser Asn Gln Thr Gln Phe Asn Gly Val Lys Val Leu Ser Gln Asp Asn Gln Met Lys Ile Gln Val Gly Ala Asn Asp Gly Glu Thr Ile Thr Ile Asp Leu Gln Lys Ile Asp Val Lys Ser Leu Gly Leu Asp Gly Phe Asn Val Asn Ser Pro Gly Ile Ser Gly Gly Gly Gly Gly Ile Leu Asp Ser Met Gly Thr Leu Ile Asn Glu Asp Ala Ala Ala Ala Lys Lys Ser Thr Ala Asn Pro Leu Ala Ser Ile Asp Ser Ala Leu Ser Lys Val Asp Ala Val Arg Ser Ser Leu Gly Ala Ile Gln Asn Arg Phe Asp Ser Ala Ile Thr Asn Leu Gly Asn Thr Val Thr Asn Leu Asn Ser Ala Arg Ser Arg Ile Glu Asp Ala Asp Tyr Ala Thr Glu Val Ser Asn Met Ser Lys Ala Gln Ile Leu Gln Gln Ala Gly Thr Ser Val Leu Ala Gln Ala Asn Gln Val Pro Gln Asn Val Leu Ser Leu Leu Arg. This protein is also known as CBLB502 (AA') as provided for in U.S. Published Patent Application No. 2009/0011982 hereby incorporated by reference. CBLB502 has been under clinical investigation to treat Acute Radiation Syndrome (ARS).

Formulations

In certain embodiments, the disclosure contemplates pharmaceutical composition comprising particles disclosed herein and a pharmaceutically acceptable excipient. The pharmaceutical composition may be in the form of a pill, tablet, capsule, or aqueous phosphate buffer solution.

Pharmaceutical compositions for use in the present disclosure typically comprise an effective amount of particles disclosed herein and a suitable pharmaceutical acceptable carrier.

Generally, for pharmaceutical use, the compounds may be formulated as a pharmaceutical preparation comprising at least one compound and at least one pharmaceutically acceptable carrier, diluent or excipient, and optionally one or more further pharmaceutically active agent.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the particles of the disclosure, e.g., about 10, 25, 50, 100, 200, 300 or 400 mg per unit dosage.

For an oral administration form, the particles can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation may additionally contain other pharmaceutical auxiliaries such as surfactants, emulsifiers and stabilizers as well as a propellant.

For subcutaneous or intravenous administration, the particles, if desired with the substances customary therefore such as solubilizers, emulsifiers or further auxiliaries are brought into solution, suspension, or emulsion. The compounds may also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the particles with a suitable non-irritating excipient, such as cocoa butter, synthetic glyceride esters or polyethylene glycols, which are solid at ordinary temperatures, but liquefy and/or dissolve in the rectal cavity.

In certain embodiments, it is contemplated that these compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethyl methacrylate)); carboxypolymethylene (for example Carbopol™); carbomer; polyvinyl pyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethyl cellulose (HMC), hydroxyethylcellulose (HEC), hydroxypropylcellulose (HPC), methylcellulose (MC), ethylcellulose (EC), carboxyethylcellulose (CEC), ethylhydroxy ethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of particles from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein delivery systems. Particles can be entrapped in the poly(lactide-co-glycolide) microsphere depot by a number of methods, including formation of a water-in-oil emulsion with water-borne particles and organic solvent-borne polymer (emulsion method), formation of a solid-in-oil suspension with solid protein dispersed in a solvent-based polymer solution (suspension method), or by dissolving the protein in a solvent-based polymer solution (dissolution method). One can attach poly(ethylene glycol) to the particles (PEGylation) to increase the in vivo half-life of circulating therapeutic proteins and decrease the chance of an immune response.

Methods of Use

In certain embodiments, the disclosure relates to methods of treating or preventing an inflammatory disease or condition, auto-immune disease, allergy, or cancer comprising administering an effective amount of a pharmaceutical composition disclosed herein to a subject in need thereof.

In certain embodiments, the inflammatory disease is inflammatory bowel disease, Crohn's disease, ulcerative colitis, proctitis, fulminant colitis, proctosigmoiditis, left-sided colitis celiac disease, or enteric infection.

In certain embodiments, the inflammatory disease or condition is selected from arthritis, heart disease, infective or non-infective endocarditis, cardiomegaly, myocarditis, chronic, or persistent, inflammatory myopathy, polymyositis, dermatomyositis, inclusion body myositis, inflammatory respiratory disease, asthma, cystic fibrosis, emphysema, chronic obstructive pulmonary disorder or acute respiratory distress syndrome.

In certain embodiments, the auto immune diseases is selected from diabetes mellitus type 1, Rheumatoid arthritis, temporal arteritis, encephalomyelitis, autoimmune cardiomyopathy, eczema, Lupus erythematosus, or Sjögren's syndrome.

In certain embodiments, the subject is in need of treatment as the subject is at risk of, exhibiting symptoms, or diagnosed with the disease or condition.

In certain embodiments, pharmaceutical comprising particles disclosed herein are administered in combination with an anti-inflammatory agent such as glucocorticoids, COX-2 inhibitors, non-steroidal anti-inflammatory drugs. Contemplated anti-inflammatory agents include, but are not limited to, aspirin, aceclofenac, advil, alclofenac, amfenac, aminophenazone, ampiroxicam, ampyrone, amtolmetin guacil, anitrazafen, azapropazone, bendazac, benzydamine, bromfenac, bumadizone, carprofen, celecoxib, cimicoxib, clofezone, clonixin, copper ibuprofenate, deracoxib, dexibuprofen, dexketoprofen, diclofenac, diclofenac/misoprostol, diflunisal, droxicam, epirizole, ethenzamide, etodolac, etofenamate, etoricoxib, famprofazone, felbinac, fenamic acid, fenbufen, fenclofenac, fenclozic acid, fenoprofen, feprazone, firocoxib, floctafenine, flumizole, flunixin, fluproquazone, flurbiprofen, ibuprofen, indomethacin, indoprofen, ketoprofen, ketorolac, licofelone, lonazolac, lornoxicam, loxoprofen, lumiracoxib, magnesium salicylate, mavacoxib, mefenamic acid, meloxicam, meseclazone, miroprofen, mofebutazone, norazone, nabumetone, naproxcinod, naproxen, nepafenac, nimesulide, oxaprozin, oxicam, oxyphenbutazone, parecoxib, phenazone, phenylbutazone, piroxicam, pirprofen, pranoprofen, proglumetacin, pulvinone, robenacoxib, rofecoxib, salicylic acid, salsalate, sulindac, suprofen, tarenflurbil, tenidap, tenoxicam, tepoxalin, tiaprofenic acid, tilmacoxib, tolfenamic acid, tolmetin, valdecoxib, vedaprofen, zomepirac, alclometasone, beclometasone dipropionate, betamethasone dipropionate, budesonide, chloroprednisone, ciclesonide, cortisol, cortisporin, cortivazol, deflazacort, dexamethasone, fludroxycortide, flunisolide, fluocinonide, fluocortolone, fluorometholone, fluticasone, hydrocortamate, megestrol acetate, meprednisone, methylprednisolone, mometasone furoate, otobiotic, paramethasone, prednisolone, prednisone, prednylidene, pregnadiene, pregnatriene, pregnene, proctosedyl, rimexolone, tetrahydrocorticosterone, tobramycin/dexamethasone, triamcinolone, ulobetasol, and combinations thereof.

In certain embodiments, this disclosure relates to methods of treating cancer comprising administering an effective amount of a pharmaceutical composition comprising particles disclosed herein to a subject in need thereof. In certain embodiments, the cancer is selected from breast, pancreatic, colon, metastatic lung cancers, bladder cancer, lung cancer, breast cancer, melanoma, colon and rectal cancer, non-hodgkin lymphoma, endometrial cancer, pancreatic cancer, kidney cancer, prostate cancer, leukemia, thyroid cancer, glioblastoma (GBM), and brain cancer. In certain embodiments, the particles are administered in combination with a second anti-cancer agent such as an agent selected from tamoxifen, gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vinblastine, vindesine, vinorelbine, taxol, temozolamide, bevacizumab, procarbazine, lomustine, vincristine, taxotere, etoposide, teniposide, amsacrine, topotecan, camptothecin, bortezomib, anagrelide, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, combretastatin, thalidomide, and/or lenalidomide or combinations thereof.

The particles can be administered by a variety of routes including the oral, ocular, rectal, transdermal, subcutaneous, intravenous, intramuscular or intranasal routes, depending mainly on the specific preparation used. The particles will generally be administered in an "effective amount", by which is meant any amount of particles that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

Examples

Nanoparticle Production and Characterization

The genes of AvrA and mutant form mAvrA were cloned into pGEX expression plasmids containing glutathione S-transferase (GST) and 6x-his tags using standard recombinant techniques. The mutant form contains a single cysteine substitution (C186A) that renders the acetyltransferase inactive and eliminates JNK inhibition. Following expression in *E. coli*, AvrA and mAvrA were column purified with GST resin under native conditions.

Protein nanoparticles were fabricated by ethanol solvation with several proteins, including AvrA, mAvrA, bovine serum albumin (BSA), green fluorescent protein (GFP), flagellin, and mixtures of these proteins. 3,3'-Dithiobis[sulfosuccinimidylpropionate] (DTSSP) was used to crosslink the particles for stability during delivery to cells. DTSSP contains a central disulfide bond that can be reduced inside cells to release individual proteins. Solvent volume, crosslinker concentration, reaction time, and use of a reaction quencher were explored to produce protein nanoparticles with diameters of ~100 nm, shown in FIG. 2A, B. Particles containing GFP were fluorescent, implying that protein structure was not significantly affected by the crosslinking.

GFP particles crosslinked with DTSSP were tested for their ability to disassemble in a reducing environment. Particles were incubated in PBS containing 0 mM, 1 mM or 10 mM glutathione at 37° C. to mimic intracellular reducing conditions. Soluble protein concentration was measured by fluorimeter. In the presence of either 1 mM or 10 mM glutathione, after 30 minutes the particles suddenly and completely disassembled, releasing soluble protein. In order to estimate the stability of the particles and proteins in the in vivo intestinal environment, soluble GFP and GFP nanoparticles were incubated in fasted intestinal simulation media (pH 6.5) with or without pancreatin for 2 hours. Fluorescence was measured to observe loss of model protein function. Soluble GFP lost twice as much fluorescence as nanoparticle GFP, with pancreatin as compared to without pancreatin. This data demonstrates the stabilizing or protective effect of the nanoparticle formulation (FIG. 2C).

Cellular Uptake and Trafficking of Nanoparticles

Nanoparticles were incubated with HeLa cells for preliminary quantification of cellular uptake. GFP was included in the nanoparticle formulation to enable assessment by fluorimetery, flow cytometry, confocal microscopy, and to compare with soluble proteins not formulated as nanoparticles. FIG. 3A shows the increase in total GFP delivered to cells by nanoparticles, as compared to free GFP molecules, measured by fluorimetry over a 5 hour incubation period. After uptake, it is important that the particles disassemble and free proteins make their way to the cytosol to bind their targets. Confocal microscopy in FIGS. 3B-D illustrate the uptake of intact particles, identified as punctate fluorescent spots, into cells and that individual (GFP) proteins are being released from the particles and diffusing into the cytosol, identified as diffuse fluorescence in the cell. Very little uptake is seen after 1 hour, while after 3 hours nanoparticles appear in cells with some diffusion, and after 6 hours most particles seem to have disassembled and diffused into the cytosol.

Effects on Pro-Inflammatory Signaling and Effectors In Vitro

Figure 4:
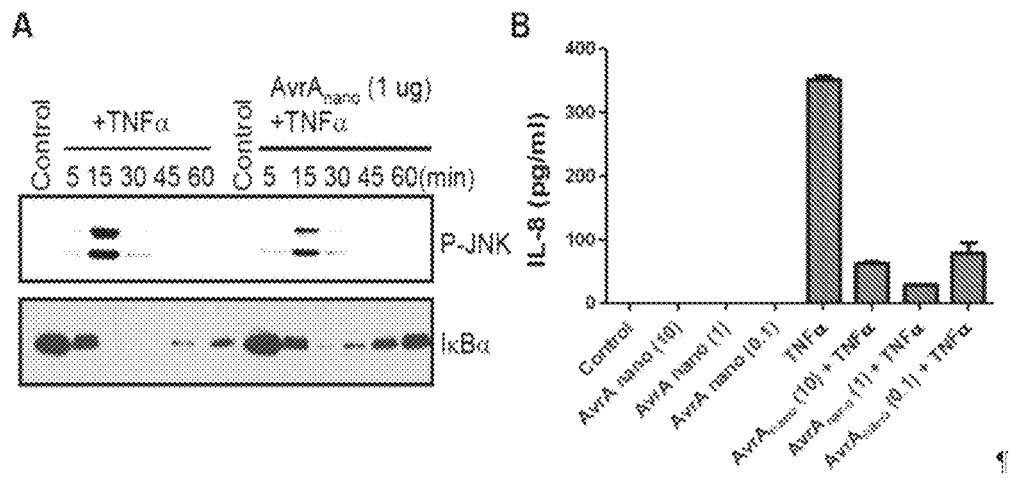
FIG. 4 shows western blots with indicated antisera (A) and IL-8 ELISA data (B) in polarized T84 monolayers. AvrA nanoparticles were applied for 3 hrs prior to TNF-α stimulation.

AvrA inhibits JNK phosphorylation and IκB degradation in transfection and transgenic approaches. Experiments with AvrA nanoparticle preparations applied to the apical surface of polarized T84 monolayers (for 3 hours to allow particle internalization and dissociation) were successful in partly suppressing both TNF-α induced JNK activation and IκB degradation (FIG. 4A). This partial suppression may reflect the amount of AvrA that occurs during natural infection. Real time imaging of a *Salmonella* model infection has shown that a different TTSS-secreted effector, SipA, mediates biochemical functions within minutes of infection at a concentration of 1000 molecules/cell. See Schlumberger et al., Proc Natl Acad Sci USA, 2005, 102(35):12548-12553. This is the target dose to achieve with modified AvrA nanoparticles. T84 monolayers incubated with AvrA nanoparticles and stimulated with TNF-α were also assayed for IL-8 secretion at 6 hours by ELISA (FIG. 4B). Secreted IL-8 was markedly reduced in particle treated cells. Collectively, the data in FIG. 4 demonstrate that the degree of JNK suppression is sufficiently strong to block transcriptional upregulation of key inflammatory mediators, and confirms the bioactivity of recombinant AvrA nanoparticles.

In Vivo Models of Inflammation

The murine peritonitis model of acute inflammation was employed. Mice were pretreated with an intraperitoneal (IP) dose of active AvrA nanoparticles, mAvrA particles, inert BSA particles or PBS control for one hour before IP instillation of 10 mg zymosan, a fungal cell wall component commonly used as an inducer of acute inflammation. After four additional hours, mice were sacrificed and inflammatory exudates in the peritoneal cavity collected by lavage. Neutrophils were marked with relevant antibodies and populations quantified by flow cytometry.

Figure 5:
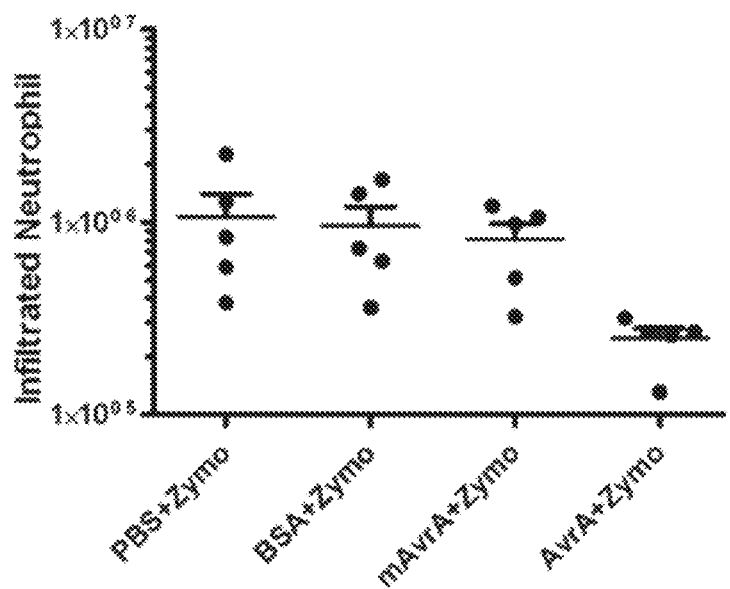
FIG. 5 shows data on the quantification of neutrophils isolated by peritoneal lavage from mice (5 per indicated condition).

As shown in FIG. 5, while essentially no inflammatory cells were detected in control (PBS treated, no zymosan) mice, positive control (PBS pretreated, zymosan) mice showed the expected accumulation of neutrophils. Strikingly, pretreatment with AvrA nanoparticles resulted in a significant reduction of neutrophil influx into the peritoneal cavity. Inert BSA particles showed no effects while mutant AvrA particles showed a reduced, statistically insignificant reduction in inflammation.

Figure 6:
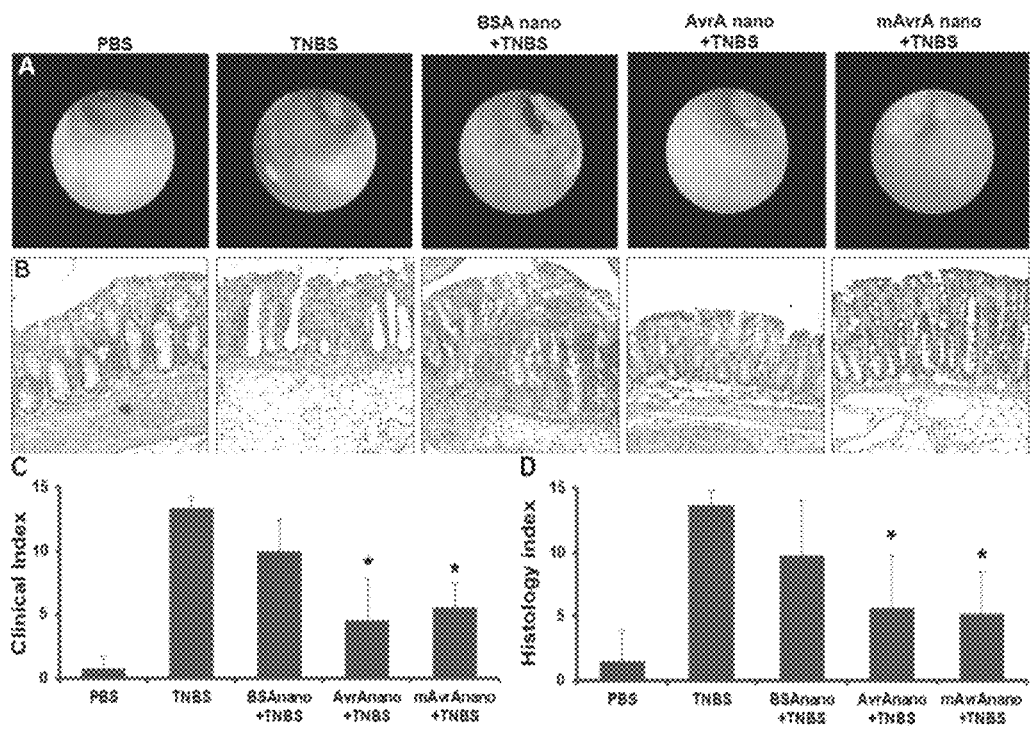
FIG. 6 shows data: (A) representative microendoscopic image of colon from mouse treated as indicated. (C) Quantification of clinical and endoscopic score from 5 five mice treated as indicated. (B) Representative colon histology from mouse treated as indicated. (D) Quantification of histological score from 5 five mice treated as indicated.

AvrA particles were tested in an in vivo model of colitis. TNBS-colitis is a rapid transmural colitis model induced by the rectal administration of the hapten reagent TNBS associated with a Th1 T cell response. Inflammatory responses can be observed within 24 hours. Whether luminal (transrectal) instillation of particles four hours prior to TNBS administration could modify this colitis model was tested. As shown in FIG. 6, at 48 hours TNBS results in marked colitis as measured by clinical parameters using a small animal veterinary endoscope and standard histological indices. Remarkably, these parameters were significantly improved in mice pretreated with the AvrA particles, while control BSA particles had no effect. Mutant AvrA particles showed significant activity suggesting the therapeutic enzymatic activity of AvrA is not abolished with a single mutation in the acetyltransferase active site. AvrA has also been shown to exhibit deubiquitinase activity that is not entirely abolished by the mutation.

The invention claimed is:

1. A method of treating an inflammatory disease comprising administering an effective amount of a pharmaceutical composition comprising particles comprising
   a) recombinant AvrA proteins; and
   b) linking groups comprising disulfide bonds,
   wherein the linking groups conjugate the recombinant AvrA proteins to form the particles, and wherein the size of the particles are between 50 nm and 200 nm in diameter, to a subject in need thereof.

2. The method of claim 1, wherein the inflammatory disease is inflammatory bowel disease, Crohn's disease, ulcerative colitis, proctitis, fulminant colitis, proctosigmoiditis, left-sided colitis celiac disease, or enteric infection.

3. The method of claim 2, wherein the subject is in need of treatment as the subject is at risk of, exhibiting symptoms, or diagnosed with an inflammatory bowel disease.

4. The method of claim 2, wherein the subject is exhibiting symptoms of abdominal pain or bloody diarrhea or combination thereof.

5. The method of claim 3, wherein the composition is administered in combination with second anti-inflammatory agent.

6. The method of claim 1, wherein the recombinant AvrA is mAvrA(C186A).

7. The method of claim 1, wherein the recombinant AvrA proteins are fusion proteins comprising bovine serum albumin (BSA), green fluorescent protein (GFP), glutathione S-transferase (GST), polyhistidine, polylysine, or combinations thereof.

8. The method of claim 1, wherein the linking groups have the following formula, $$L\overset{O}{\underset{}{\|}}{-}(X)n{-}S{-}S{-}(X)n{-}\overset{}{\underset{O}{\|}}L$$

wherein,
n is 1 to 100,
L forms amides to the recombinant AvrA proteins, and
X is at each occurrence individually and independently selected from O, NH, C=O, $CH_2$, $OCH_2$, $CH_2O$, $NHCH_2$, $CH_2NH$, $OCH_2CH_2$, $CH_2CH_2O$, $NHCH_2CH_2$, or $CH_2CH_2NH$.

9. The method of claim 8, wherein X is $(CH_2)n$ wherein n is 1 to 4.

* * * * *

SEQUENCE LISTING

<160> NUMBER OF SEQ ID NOS: 35

<210> SEQ ID NO 1
<211> LENGTH: 301
<212> TYPE: PRT
<213> ORGANISM: Salmonella enterica

<400> SEQUENCE: 1

Met Ile Phe Ser Val Gln Glu Leu Ser Cys Gly Gly Lys Ser Met Leu
1               5                   10                  15

Ser Pro Thr Thr Arg Asn Met Gly Ala Ser Leu Ser Pro Gln Pro Asp
            20                  25                  30

```
Val Ser Gly Glu Leu Asn Thr Glu Ala Leu Thr Cys Ile Val Glu Arg
         35                  40                  45

Leu Glu Ser Glu Ile Ile Asp Gly Ser Trp Ile His Ile Ser Tyr Glu
 50                  55                  60

Glu Thr Asp Leu Glu Met Met Pro Phe Leu Val Ala Gln Ala Asn Lys
65                   70                  75                  80

Lys Tyr Pro Glu Leu Asn Leu Lys Phe Val Met Ser Val His Glu Leu
                 85                  90                  95

Val Ser Ser Ile Lys Glu Thr Arg Met Glu Gly Val Glu Ser Ala Arg
             100                 105                 110

Phe Leu Val Asn Met Gly Ser Ser Gly Ile His Ile Ser Val Val Asp
             115                 120                 125

Phe Arg Val Met Asp Gly Lys Thr Ser Val Ile Leu Phe Glu Pro Ala
130                 135                 140

Ala Cys Ser Ala Phe Gly Pro Ala Leu Ala Leu Arg Thr Lys Ala Ala
145                 150                 155                 160

Leu Glu Arg Glu Gln Leu Pro Asp Cys Tyr Phe Ala Met Val Glu Leu
                 165                 170                 175

Asp Ile Gln Arg Ser Ser Glu Cys Gly Ile Phe Ser Leu Ala Leu
             180                 185                 190

Ala Lys Lys Leu Gln Leu Glu Phe Met Asn Leu Val Lys Ile His Glu
             195                 200                 205

Asp Asn Ile Cys Glu Arg Leu Cys Gly Glu Glu Pro Phe Leu Pro Ser
             210                 215                 220

Asp Lys Ala Asp Arg Tyr Leu Pro Val Ser Phe Tyr Lys His Thr Gln
225                 230                 235                 240

Gly Ala Gln Arg Leu Asn Glu Tyr Val Glu Ala Asn Pro Ala Ala Gly
                 245                 250                 255

Ser Ser Ile Val Asn Lys Lys Asn Glu Thr Leu Tyr Glu Arg Phe Asp
             260                 265                 270

Asn Asn Ala Val Met Leu Asn Asp Lys Lys Leu Ser Ile Ser Ala His
             275                 280                 285

Lys Lys Arg Ile Ala Glu Tyr Lys Ser Leu Leu Lys Pro
        290                 295                 300

<210> SEQ ID NO 2
<211> LENGTH: 288
<212> TYPE: PRT
<213> ORGANISM: Salmonella enterica

<400> SEQUENCE: 2

Met Leu Ser Pro Thr Ala Arg Asn Met Gly Ala Ser Leu Ser Pro Gln
1               5                   10                  15

Pro Asp Val Ser Gly Glu Leu Asn Thr Glu Ala Leu Thr Cys Ile Val
             20                  25                  30

Glu Arg Leu Glu Ser Glu Ile Ile Asp Gly Ser Trp Ile His Ile Ser
             35                  40                  45

Tyr Glu Glu Thr Asp Leu Glu Met Met Pro Phe Leu Val Ala Gln Ala
 50                  55                  60

Asn Lys Lys Tyr Pro Glu Leu Asn Leu Lys Phe Val Met Ser Val His
65                   70                  75                  80

Glu Leu Val Ser Ser Ile Lys Glu Thr Arg Met Glu Gly Val Glu Ser
                 85                  90                  95

Ala Arg Phe Ile Val Asn Met Gly Ser Ser Gly Ile His Ile Ser Val
             100                 105                 110
```

-continued

```
Val Asp Phe Arg Val Met Asp Gly Lys Thr Ser Val Ile Leu Phe Glu
            115                 120                 125

Pro Ala Ala Cys Ser Ala Phe Gly Pro Ala Leu Leu Ala Leu Arg Thr
        130                 135                 140

Lys Ala Ala Leu Glu Arg Glu Gln Leu Pro Asp Cys Tyr Phe Ala Met
145                 150                 155                 160

Val Glu Leu Asp Ile Gln Arg Ser Ser Glu Cys Gly Ile Phe Ser
            165                 170                 175

Leu Ala Leu Ala Lys Lys Leu Gln Leu Glu Phe Met Asn Leu Val Lys
            180                 185                 190

Ile His Glu Asp Asn Ile Cys Glu Arg Leu Cys Gly Glu Glu Pro Phe
            195                 200                 205

Leu Pro Ser Asp Lys Ala Asp Arg Tyr Leu Pro Val Ser Phe Tyr Lys
        210                 215                 220

His Thr Gln Gly Val Gln Arg Leu Asn Glu Tyr Val Gln Ala Asn Pro
225                 230                 235                 240

Ala Ala Gly Ser Ser Ile Val Asn Lys Lys Asn Glu Thr Leu Tyr Glu
            245                 250                 255

Arg Phe Asp Asn Asn Ala Val Met Leu Asn Asp Lys Lys Leu Ser Ile
            260                 265                 270

Ser Ala His Lys Lys Arg Ile Ala Glu Tyr Lys Ser Leu Leu Lys Pro
            275                 280                 285
```

<210> SEQ ID NO 3
<211> LENGTH: 289
<212> TYPE: PRT
<213> ORGANISM: Artificial
<220> FEATURE:
<223> OTHER INFORMATION: Synthetic

<400> SEQUENCE: 3

```
Met Lys Val Asn Leu Glu Gln Asn His Tyr Tyr Glu Gln Arg Gly Gly
1               5                   10                  15

Ser Asp Leu Arg Glu Gln Leu Ser Ser Tyr Ile Asp Leu Met Asp Asp
            20                  25                  30

Ala Ile Arg Gln Gly Lys Gln Leu Pro Lys Asp Thr Ala Ala Ala Asn
        35                  40                  45

Asp Ile Ala Leu Met Asp Asp Phe Ile Ala Ile Ala Asn Gln Lys Lys
    50                  55                  60

Glu Gly Leu Asn Ala His Phe Phe Arg Ser Pro Leu Asp Met Val Asn
65                  70                  75                  80

Tyr Val Lys Ser Leu Ile Pro Ser Glu Asp Thr Thr Ala Arg Phe Val
            85                  90                  95

Val Asn Met Gly Ser Gly Gly Ile His Cys Ile Ala Val Asp Cys Ala
            100                 105                 110

Ile Lys Asn Gly Lys Cys Ser Leu Ile Gly Ile Glu Pro Val Thr Met
        115                 120                 125

Asn Ser Leu Gly Ala Ser Met Leu Ala Ile Arg Leu Gln Ser Val Cys
    130                 135                 140

Lys Arg Glu Leu Pro Glu Thr Ser Leu Val Ile Met Glu Thr Asp Met
145                 150                 155                 160

Gln Arg Ser Gln Gly Glu Cys Leu Met Phe Ser Leu Phe Leu Val Lys
            165                 170                 175

Lys Met His Lys Glu Cys Asp Glu Phe Gln Tyr Leu His Asp Lys Asn
            180                 185                 190
```

```
Ile Asn Arg Glu Leu Pro Leu Thr Gln Gly Leu Ile Val Ser Val Lys
            195                 200                 205

Asp Ala Asp Ser Leu Leu Pro Pro Ser Leu Met Lys His Thr Gln Ser
    210                 215                 220

Pro Asn Arg Leu Gln Lys Tyr Leu Glu Met Arg Pro Glu Ala Met Asn
225                 230                 235                 240

Cys Val Val Asn Lys Lys Gly Glu Thr Leu Lys Thr Arg Gln Gln Arg
                245                 250                 255

His Ile Thr Thr Ile Glu Leu Gly Lys Thr Val Ser Tyr Ser Asn
            260                 265                 270

Ser Ile Glu Gln Lys Arg Ile Lys Glu Ala Lys Gly Leu Leu Asn Asn
            275                 280                 285

Leu

<210> SEQ ID NO 4
<211> LENGTH: 216
<212> TYPE: PRT
<213> ORGANISM: Artificial
<220> FEATURE:
<223> OTHER INFORMATION: Synthetic

<400> SEQUENCE: 4

Asn Asp Ile Ala Leu Ile Pro Asp Phe Ile Asp Ile Ala Asn Lys Lys
1               5                   10                  15

Lys Ala Gly Leu Asn Ala Ile Phe Cys Asn Asn Pro Leu Glu Met Val
            20                  25                  30

Glu Lys Val Lys Gln Leu Leu Leu Leu Glu Asn Ser Ser Ala Arg Phe
        35                  40                  45

Ile Val Asn Leu Gly Cys Gly Gly Ile His Cys Met Ala Val Asp Cys
    50                  55                  60

Leu Val Ser Asp Gly Lys Cys Ser Leu Ile Gly Ile Glu Pro Val Gly
65                  70                  75                  80

Met Asn Ser Ser Gly Pro Ala Leu Leu Ala Ile Arg Leu Gln Ser Ile
                85                  90                  95

Cys Lys Arg Glu Leu Pro Glu Ala Ala Leu Ala Ile Phe Glu Thr Asp
            100                 105                 110

Met Gln Arg Ser Tyr Gly Glu Cys Ala Met Phe Ser Leu Phe Leu Val
        115                 120                 125

Lys Lys Met His Lys Glu Ser Ala Gln Phe Gln Glu Leu His Lys Lys
    130                 135                 140

Asn Ile Asp Gln Asn Leu Pro Lys Ser Gly Glu Ile Ile Val Ser Val
145                 150                 155                 160

Ser Gln Thr Asn Asn Leu Leu Pro Pro Ser Leu Met Lys His Val Gln
                165                 170                 175

Ser Pro Lys Arg Leu Glu Ala Tyr Leu Glu Ser Arg Pro Glu Ala Ala
            180                 185                 190

Asp Val Val Val Asn Lys Lys Gly Glu Thr Leu Leu Ser Arg Gln Gln
        195                 200                 205

Arg Tyr Ile Ala Thr Ile Glu Ala
    210                 215

<210> SEQ ID NO 5
<211> LENGTH: 299
<212> TYPE: PRT
<213> ORGANISM: Artificial
<220> FEATURE:
```

<223> OTHER INFORMATION: Synthetic

<400> SEQUENCE: 5

Met Asn Ile Pro Pro Ile His Ile Lys Thr Asp Leu Thr Asn Gln Asp
1               5                   10                  15

Glu Lys Thr Thr Ile Gln Glu Ala Thr Lys Glu Glu Leu Gln Leu Leu
            20                  25                  30

Ile Ala Thr Met Glu Arg Glu Leu Ala Ser Gly Glu Phe Phe Thr Ser
        35                  40                  45

His Glu Asn Tyr Ala Ser Ile Asp Leu Gly Lys Met Pro Leu Leu Ile
    50                  55                  60

Glu Ala Ala Asn Asn Lys His Val Gly Leu Asn Leu Asn Phe Val Ser
65                  70                  75                  80

Asn Pro Ile Asp Leu Pro Ser Glu Ile Gly Arg Ala Ile Ser Asn Gly
                85                  90                  95

Lys Glu Gln Phe Arg Tyr Val Val Asn Met Gly Glu Ser Gly Ile His
            100                 105                 110

Phe Ala Ala Ile Asp Cys Lys Met Val Asp Gly Lys Leu Ser Leu Leu
        115                 120                 125

Leu Met Glu Pro Ala Asn Leu Asn Ser Met Gly Pro Ala Met Leu Ala
    130                 135                 140

Met Arg Val Ser Ser Cys Leu Lys Arg Glu Ala Glu Ile Ile Pro Lys
145                 150                 155                 160

Pro His Phe Cys Ile Ala Val Met Asp Ile Gln Arg Ser Asn Ser Glu
                165                 170                 175

Cys Gly Ile Phe Ser Val Gly Leu Ala Lys Lys Met Phe Ser Glu Arg
            180                 185                 190

Ala Pro Leu Asp Ala Leu His Glu Glu Ile Leu Ser Glu Arg Leu Pro
        195                 200                 205

Asp Gly Met Lys Cys Asp Val Leu Gly Glu Ala Leu Asp Arg Leu
    210                 215                 220

Leu Pro Pro Thr Phe Tyr Lys His Ala Gln Ser Gln Arg Arg Leu Asp
225                 230                 235                 240

Gln Tyr Ile Arg Ala His Pro Asp Gly Asn Asp Thr Ser Val Asn Lys
                245                 250                 255

Lys Gly Glu Leu Leu Leu Asp Arg Ala Lys Arg Leu Met Val Pro Val
            260                 265                 270

Asp Glu Lys Leu Ile Ser Ser Ser Ile His Gln Lys Arg Ile Met Glu
        275                 280                 285

Tyr Ser Ala Ile Ser Asp Asp Gly Lys Ser Val
    290                 295

<210> SEQ ID NO 6
<211> LENGTH: 101
<212> TYPE: PRT
<213> ORGANISM: Artificial
<220> FEATURE:
<223> OTHER INFORMATION: Synthetic

<400> SEQUENCE: 6

Met Glu Pro Val Asp Pro Arg Leu Glu Pro Trp Lys His Pro Gly Ser
1               5                   10                  15

Gln Pro Lys Thr Pro Cys Thr Lys Cys Tyr Cys Lys Lys Cys Cys Leu
            20                  25                  30

His Cys Gln Val Cys Phe Met Thr Lys Gly Leu Gly Ile Ser Tyr Gly
        35                  40                  45

```
Arg Lys Lys Arg Arg Gln Arg Arg Ala Pro Gln Asp Asn Lys Asn
    50                  55                  60

His Gln Val Ser Leu Ser Lys Gln Pro Thr Ser Arg Ala Arg Gly Asp
 65                  70                  75                  80

Pro Thr Gly Gln Glu Glu Ser Lys Glu Lys Val Glu Lys Glu Thr Val
                 85                  90                  95

Val Asp Pro Val Thr
            100

<210> SEQ ID NO 7
<211> LENGTH: 7
<212> TYPE: PRT
<213> ORGANISM: Artificial
<220> FEATURE:
<223> OTHER INFORMATION: Synthetic

<400> SEQUENCE: 7

Phe Phe Leu Ile Pro Lys Gly
1               5

<210> SEQ ID NO 8
<211> LENGTH: 15
<212> TYPE: PRT
<213> ORGANISM: Artificial
<220> FEATURE:
<223> OTHER INFORMATION: Synthetic

<400> SEQUENCE: 8

Phe Phe Leu Ile Pro Lys Gly Arg Arg Arg Arg Arg Arg Arg Arg
1               5                  10                  15

<210> SEQ ID NO 9
<211> LENGTH: 7
<212> TYPE: PRT
<213> ORGANISM: Artificial
<220> FEATURE:
<223> OTHER INFORMATION: Synthetic

<400> SEQUENCE: 9

Gly Lys Pro Ile Leu Phe Phe
1               5

<210> SEQ ID NO 10
<211> LENGTH: 15
<212> TYPE: PRT
<213> ORGANISM: Artificial
<220> FEATURE:
<223> OTHER INFORMATION: Synthetic

<400> SEQUENCE: 10

Arg Arg Arg Arg Arg Arg Arg Arg Gly Lys Pro Ile Leu Phe Phe
1               5                  10                  15

<210> SEQ ID NO 11
<211> LENGTH: 55
<212> TYPE: PRT
<213> ORGANISM: Artificial
<220> FEATURE:
<223> OTHER INFORMATION: Synthetic

<400> SEQUENCE: 11

Gly Ala Leu Phe Leu Gly Phe Leu Gly Ala Ala Ala Ala Ala Ala
1               5                  10                  15

Ala Ala Ala Ala Gly Ser Thr Met Gly Ala Trp Ser Gln Gln Gln Gln
```

```
                        20                  25                  30

Gln Gln Gln Gln Gln Gln Gln Gln Gln Gln Gln Gln Gln Gln Gln
                35                  40                  45

Pro Lys Lys Lys Arg Lys Val
        50                  55

<210> SEQ ID NO 12
<211> LENGTH: 55
<212> TYPE: PRT
<213> ORGANISM: Artificial
<220> FEATURE:
<223> OTHER INFORMATION: Synthetic

<400> SEQUENCE: 12

Gly Ala Leu Phe Leu Ala Phe Leu Ala Ala Ala Ala Ala Ala Ala
1               5                   10                  15

Ala Ala Ala Ala Leu Ser Leu Met Gly Leu Trp Ser Gln Gln Gln
                20                  25                  30

Gln Gln Gln Gln Gln Gln Gln Gln Gln Gln Gln Gln Gln Gln Gln
                35                  40                  45

Pro Lys Lys Lys Arg Lys Val
        50                  55

<210> SEQ ID NO 13
<211> LENGTH: 16
<212> TYPE: PRT
<213> ORGANISM: Artificial
<220> FEATURE:
<223> OTHER INFORMATION: Synthetic

<400> SEQUENCE: 13

Arg Val Ile Arg Val Trp Phe Gln Asn Lys Arg Cys Lys Asp Lys Lys
1               5                   10                  15

<210> SEQ ID NO 14
<211> LENGTH: 16
<212> TYPE: PRT
<213> ORGANISM: Artificial
<220> FEATURE:
<223> OTHER INFORMATION: Synthetic

<400> SEQUENCE: 14

Arg Gln Ile Lys Ile Trp Phe Gln Asn Arg Arg Met Lys Trp Lys Lys
1               5                   10                  15

<210> SEQ ID NO 15
<211> LENGTH: 28
<212> TYPE: PRT
<213> ORGANISM: Artificial
<220> FEATURE:
<223> OTHER INFORMATION: Synthetic

<400> SEQUENCE: 15

Gly Trp Thr Leu Asn Ser Ala Gly Tyr Leu Leu Gly Lys Ile Asn Leu
1               5                   10                  15

Lys Ala Leu Leu Ala Ala Leu Ala Lys Lys Ile Leu
                20                  25

<210> SEQ ID NO 16
<211> LENGTH: 698
<212> TYPE: PRT
<213> ORGANISM: Artificial
<220> FEATURE:
<223> OTHER INFORMATION: Synthetic
```

```
<400> SEQUENCE: 16

Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45

Ile Pro Ser Asp Gly Pro Ser Val Ala Cys Val Lys Lys Ala Ser Tyr
    50                  55                  60

Leu Asp Cys Ile Arg Ala Ile Ala Ala Asn Glu Ala Asp Ala Val Thr
65                  70                  75                  80

Leu Asp Ala Gly Leu Val Tyr Asp Ala Tyr Leu Ala Pro Asn Asn Leu
                85                  90                  95

Lys Pro Val Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met
        115                 120                 125

Asn Gln Leu Arg Gly Lys Lys Ser Cys His Thr Gly Leu Gly Arg Ser
    130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
            180                 185                 190

Cys Pro Gly Cys Gly Cys Ser Thr Leu Asn Gln Tyr Phe Gly Tyr Ser
        195                 200                 205

Gly Ala Phe Lys Cys Leu Lys Asp Gly Ala Gly Asp Val Ala Phe Val
    210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
            260                 265                 270

Arg Ser Met Gly Gly Lys Glu Asp Leu Ile Trp Glu Leu Leu Asn Gln
        275                 280                 285

Ala Gln Glu His Phe Gly Lys Asp Lys Ser Lys Glu Phe Gln Leu Phe
    290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335

Glu Tyr Val Thr Ala Ile Arg Asn Leu Arg Glu Gly Thr Cys Pro Glu
            340                 345                 350

Ala Pro Thr Asp Glu Cys Lys Pro Val Lys Trp Cys Ala Leu Ser His
        355                 360                 365

His Glu Arg Leu Lys Cys Asp Glu Trp Ser Val Asn Ser Val Gly Lys
    370                 375                 380

Ile Glu Cys Val Ser Ala Glu Thr Thr Glu Asp Cys Ile Ala Lys Ile
385                 390                 395                 400

Met Asn Gly Glu Ala Asp Ala Met Ser Leu Asp Gly Gly Phe Val Tyr
```

```
              405                 410                 415
Ile Ala Gly Lys Cys Gly Leu Val Pro Val Leu Ala Glu Asn Tyr Asn
            420                 425                 430

Lys Ser Asp Asn Cys Glu Asp Thr Pro Glu Ala Gly Tyr Phe Ala Val
        435                 440                 445

Ala Val Val Lys Lys Ser Ala Ser Asp Leu Thr Trp Asp Asn Leu Lys
    450                 455                 460

Gly Lys Lys Ser Cys His Thr Ala Val Gly Arg Thr Ala Gly Trp Asn
465                 470                 475                 480

Ile Pro Met Gly Leu Leu Tyr Asn Lys Ile Asn His Cys Arg Phe Asp
                485                 490                 495

Glu Phe Phe Ser Glu Gly Cys Ala Pro Gly Ser Lys Lys Asp Ser Ser
            500                 505                 510

Leu Cys Lys Leu Cys Met Gly Ser Gly Leu Asn Leu Cys Glu Pro Asn
        515                 520                 525

Asn Lys Glu Gly Tyr Tyr Gly Tyr Thr Gly Ala Phe Arg Cys Leu Val
    530                 535                 540

Glu Lys Gly Asp Val Ala Phe Val Lys His Gln Thr Val Pro Gln Asn
545                 550                 555                 560

Thr Gly Gly Lys Asn Pro Asp Pro Trp Ala Lys Asn Leu Asn Glu Lys
                565                 570                 575

Asp Tyr Glu Leu Leu Cys Leu Asp Gly Thr Arg Lys Pro Val Glu Glu
            580                 585                 590

Tyr Ala Asn Cys His Leu Ala Arg Ala Pro Asn His Ala Val Val Thr
        595                 600                 605

Arg Lys Asp Lys Glu Ala Cys Val His Lys Ile Leu Arg Gln Gln Gln
    610                 615                 620

His Leu Phe Gly Ser Asn Val Thr Asp Cys Ser Gly Asn Phe Cys Leu
625                 630                 635                 640

Phe Arg Ser Glu Thr Lys Asp Leu Leu Phe Arg Asp Asp Thr Val Cys
                645                 650                 655

Leu Ala Lys Leu His Asp Arg Asn Thr Tyr Glu Lys Tyr Leu Gly Glu
            660                 665                 670

Glu Tyr Val Lys Ala Val Gly Asn Leu Arg Lys Cys Ser Thr Ser Ser
        675                 680                 685

Leu Leu Glu Ala Cys Thr Phe Arg Arg Pro
    690                 695

<210> SEQ ID NO 17
<211> LENGTH: 679
<212> TYPE: PRT
<213> ORGANISM: Artificial
<220> FEATURE:
<223> OTHER INFORMATION: Synthetic

<400> SEQUENCE: 17

Val Pro Asp Lys Thr Val Arg Trp Cys Ala Val Ser Glu His Glu Ala
1               5                   10                  15

Thr Lys Cys Gln Ser Phe Arg Asp His Met Lys Ser Val Ile Pro Ser
            20                  25                  30

Asp Gly Pro Ser Val Ala Cys Val Lys Lys Ala Ser Tyr Leu Asp Cys
        35                  40                  45

Ile Arg Ala Ile Ala Ala Asn Glu Ala Asp Ala Val Thr Leu Asp Ala
    50                  55                  60

Gly Leu Val Tyr Asp Ala Tyr Leu Ala Pro Asn Asn Leu Lys Pro Val
```

-continued

```
                65                  70                  75                  80
Val Ala Glu Phe Tyr Gly Ser Lys Glu Asp Pro Gln Thr Phe Tyr Tyr
                    85                  90                  95

Ala Val Ala Val Val Lys Lys Asp Ser Gly Phe Gln Met Asn Gln Leu
                100                 105                 110

Arg Gly Lys Lys Ser Cys His Thr Gly Leu Gly Arg Ser Ala Gly Trp
                115                 120                 125

Asn Ile Pro Ile Gly Leu Leu Tyr Cys Asp Leu Pro Glu Pro Arg Lys
            130                 135                 140

Pro Leu Glu Lys Ala Val Ala Asn Phe Phe Ser Gly Ser Cys Ala Pro
145                 150                 155                 160

Cys Ala Asp Gly Thr Asp Phe Pro Gln Leu Cys Gln Leu Cys Pro Gly
                    165                 170                 175

Cys Gly Cys Ser Thr Leu Asn Gln Tyr Phe Gly Tyr Ser Gly Ala Phe
                180                 185                 190

Lys Cys Leu Lys Asp Gly Ala Gly Asp Val Ala Phe Val Lys His Ser
            195                 200                 205

Thr Ile Phe Glu Asn Leu Ala Asn Lys Ala Asp Arg Asp Gln Tyr Glu
        210                 215                 220

Leu Leu Cys Leu Asp Asn Thr Arg Lys Pro Val Asp Glu Tyr Lys Asp
225                 230                 235                 240

Cys His Leu Ala Gln Val Pro Ser His Thr Val Val Ala Arg Ser Met
                    245                 250                 255

Gly Gly Lys Glu Asp Leu Ile Trp Glu Leu Leu Asn Gln Ala Gln Glu
                260                 265                 270

His Phe Gly Lys Asp Lys Ser Lys Glu Phe Gln Leu Phe Ser Ser Pro
            275                 280                 285

His Gly Lys Asp Leu Leu Phe Lys Asp Ser Ala His Gly Phe Leu Lys
        290                 295                 300

Val Pro Pro Arg Met Asp Ala Lys Met Tyr Leu Gly Tyr Glu Tyr Val
305                 310                 315                 320

Thr Ala Ile Arg Asn Leu Arg Glu Gly Thr Cys Pro Glu Ala Pro Thr
                    325                 330                 335

Asp Glu Cys Lys Pro Val Lys Trp Cys Ala Leu Ser His His Glu Arg
                340                 345                 350

Leu Lys Cys Asp Glu Trp Ser Val Asn Ser Val Gly Lys Ile Glu Cys
            355                 360                 365

Val Ser Ala Glu Thr Thr Glu Asp Cys Ile Ala Lys Ile Met Asn Gly
        370                 375                 380

Glu Ala Asp Ala Met Ser Leu Asp Gly Gly Phe Val Tyr Ile Ala Gly
385                 390                 395                 400

Lys Cys Gly Leu Val Pro Val Leu Ala Glu Asn Tyr Asn Lys Ala Asp
                    405                 410                 415

Asn Cys Glu Asp Thr Pro Glu Ala Gly Tyr Phe Ala Val Ala Val Val
                420                 425                 430

Lys Lys Ser Ala Ser Asp Leu Thr Trp Asp Asn Leu Lys Gly Lys Lys
            435                 440                 445

Ser Cys His Thr Ala Val Gly Arg Thr Ala Gly Trp Asn Ile Pro Met
        450                 455                 460

Gly Leu Leu Tyr Asn Lys Ile Asn His Cys Arg Phe Asp Glu Phe Phe
465                 470                 475                 480

Ser Glu Gly Cys Ala Pro Gly Ser Lys Lys Asp Ser Ser Leu Cys Lys
                    485                 490                 495
```

```
Leu Cys Met Gly Ser Gly Leu Asn Leu Cys Glu Pro Asn Asn Lys Glu
            500                 505                 510

Gly Tyr Tyr Gly Tyr Thr Gly Ala Phe Arg Cys Leu Val Glu Lys Gly
        515                 520                 525

Asp Val Ala Phe Val Lys His Gln Thr Val Pro Gln Asn Thr Gly Gly
    530                 535                 540

Lys Asn Pro Asp Pro Trp Ala Lys Asn Leu Asn Glu Lys Asp Tyr Glu
545                 550                 555                 560

Leu Leu Cys Leu Asp Gly Thr Arg Lys Pro Val Glu Tyr Ala Asn
            565                 570                 575

Cys His Leu Ala Arg Ala Pro Asn His Ala Val Val Thr Arg Lys Asp
            580                 585                 590

Lys Glu Ala Cys Val His Lys Ile Leu Arg Gln Gln Gln His Leu Phe
        595                 600                 605

Gly Ser Asn Val Ala Asp Cys Ser Gly Asn Phe Cys Leu Phe Arg Ser
    610                 615                 620

Glu Thr Lys Asp Leu Leu Phe Arg Asp Asp Thr Val Cys Leu Ala Lys
625                 630                 635                 640

Leu His Asp Arg Asn Thr Tyr Glu Lys Tyr Leu Gly Glu Glu Tyr Val
            645                 650                 655

Lys Ala Val Gly Asn Leu Arg Lys Cys Ser Thr Ser Ser Leu Leu Glu
            660                 665                 670

Ala Cys Thr Pro Arg Arg Pro
        675

<210> SEQ ID NO 18
<211> LENGTH: 25
<212> TYPE: PRT
<213> ORGANISM: Artificial
<220> FEATURE:
<223> OTHER INFORMATION: Synthetic
<220> FEATURE:
<221> NAME/KEY: misc_feature
<223> OTHER INFORMATION: X is palmitoyl group anchored to a synthetic
      diaminopropionic acid (Dap) residue
<220> FEATURE:
<221> NAME/KEY: misc_feature
<222> LOCATION: (3)..(3)
<223> OTHER INFORMATION: Xaa can be any naturally occurring amino acid

<400> SEQUENCE: 18

Trp Gly Xaa Val Lys Ile Lys Lys Pro Pro Pro Pro Pro Pro Pro Pro
1               5                   10                  15

Pro Gly Gly His His His His His His
            20                  25

<210> SEQ ID NO 19
<211> LENGTH: 23
<212> TYPE: PRT
<213> ORGANISM: Artificial
<220> FEATURE:
<223> OTHER INFORMATION: Synthetic

<400> SEQUENCE: 19

Gly Leu Phe Glu Ala Ile Ala Gly Phe Ile Glu Asn Gly Trp Glu Gly
1               5                   10                  15

Met Ile Asp Gly Gly Gly Cys
            20

<210> SEQ ID NO 20
```

<211> LENGTH: 495
<212> TYPE: PRT
<213> ORGANISM: Salmonella typhimurium

<400> SEQUENCE: 20

```
Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
        195                 200                 205

Gly Leu Gly Gly Thr Asp Gln Lys Ile Asp Gly Asp Leu Lys Phe Asp
    210                 215                 220

Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
                245                 250                 255

Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
        275                 280                 285

Leu Thr Glu Ala Lys Ala Ala Leu Thr Ala Ala Gly Val Thr Gly Thr
    290                 295                 300

Ala Ser Val Val Lys Met Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
                325                 330                 335

Gln Asn Lys Asp Gly Ser Ile Ser Ile Asn Thr Thr Lys Tyr Thr Ala
            340                 345                 350

Asp Asp Gly Thr Ser Lys Thr Ala Leu Asn Lys Leu Gly Gly Ala Asp
        355                 360                 365

Gly Lys Thr Glu Val Val Ser Ile Gly Gly Lys Thr Tyr Ala Ala Ser
    370                 375                 380

Lys Ala Glu Gly His Asn Phe Lys Ala Gln Pro Asp Leu Ala Glu Ala
```

```
                385                 390                 395                 400
Ala Ala Thr Thr Thr Glu Asn Pro Leu Gln Lys Ile Asp Ala Ala Leu
                    405                 410                 415

Ala Gln Val Asp Thr Leu Arg Ser Asp Leu Gly Ala Val Gln Asn Arg
                420                 425                 430

Phe Asn Ser Ala Ile Thr Asn Leu Gly Asn Thr Val Asn Asn Leu Thr
                435                 440                 445

Ser Ala Arg Ser Arg Ile Glu Asp Ser Asp Tyr Ala Thr Glu Val Ser
                450                 455                 460

Asn Met Ser Arg Ala Gln Ile Leu Gln Gln Ala Gly Thr Ser Val Leu
465                 470                 475                 480

Ala Gln Ala Asn Gln Val Pro Gln Asn Val Leu Ser Leu Leu Arg
                485                 490                 495

<210> SEQ ID NO 21
<211> LENGTH: 398
<212> TYPE: PRT
<213> ORGANISM: Salmonella typhimurium

<400> SEQUENCE: 21

Phe Thr Ala Asn Ile Lys Gly Leu Thr Gln Ala Ser Arg Asn Ala Asn
1               5                   10                  15

Asp Gly Ile Ser Ile Ala Gln Thr Thr Glu Gly Ala Leu Asn Glu Ile
                20                  25                  30

Asn Asn Asn Leu Gln Arg Val Arg Glu Leu Ala Val Gln Ser Ala Asn
            35                  40                  45

Ser Thr Asn Ser Gln Ser Asp Leu Asp Ser Ile Gln Ala Glu Ile Thr
        50                  55                  60

Gln Arg Leu Asn Glu Ile Asp Arg Val Ser Gly Gln Thr Gln Phe Asn
65                  70                  75                  80

Gly Val Lys Val Leu Ala Gln Asp Asn Thr Leu Thr Ile Gln Val Gly
                85                  90                  95

Ala Asn Asp Gly Glu Thr Ile Asp Ile Asp Leu Lys Gln Ile Asn Ser
                100                 105                 110

Gln Thr Leu Gly Leu Asp Thr Leu Asn Val Gln Gln Lys Tyr Lys Val
            115                 120                 125

Ser Asp Thr Ala Ala Thr Val Thr Gly Tyr Ala Asp Thr Thr Ile Ala
        130                 135                 140

Leu Asp Asn Ser Thr Phe Lys Ala Ser Ala Thr Gly Leu Gly Gly Thr
145                 150                 155                 160

Asp Gln Lys Ile Asp Gly Asp Leu Lys Phe Asp Asp Thr Thr Gly Lys
                165                 170                 175

Tyr Tyr Ala Lys Val Thr Val Thr Gly Gly Thr Gly Lys Asp Gly Tyr
                180                 185                 190

Tyr Glu Val Ser Val Asp Lys Thr Asn Gly Glu Val Thr Leu Ala Gly
            195                 200                 205

Gly Ala Thr Ser Pro Leu Thr Gly Gly Leu Pro Ala Thr Ala Thr Glu
        210                 215                 220

Asp Val Lys Asn Val Gln Val Ala Asn Ala Asp Leu Thr Glu Ala Lys
225                 230                 235                 240

Ala Ala Leu Thr Ala Ala Gly Val Thr Gly Thr Ala Ser Val Val Lys
                245                 250                 255

Met Ser Tyr Thr Asp Asn Asn Gly Lys Thr Ile Asp Gly Gly Leu Ala
                260                 265                 270
```

-continued

Val Lys Val Gly Asp Asp Tyr Tyr Ser Ala Thr Gln Asn Lys Asp Gly
            275                 280                 285

Ser Ile Ser Ile Asn Thr Thr Lys Tyr Thr Ala Asp Asp Gly Thr Ser
290                 295                 300

Lys Thr Ala Leu Asn Lys Leu Gly Gly Ala Asp Gly Lys Thr Glu Val
305                 310                 315                 320

Val Ser Ile Gly Gly Lys Thr Tyr Ala Ala Ser Lys Ala Glu Gly His
                325                 330                 335

Asn Phe Lys Ala Gln Pro Asp Leu Ala Glu Ala Ala Thr Thr Thr
            340                 345                 350

Glu Asn Pro Leu Gln Lys Ile Asp Ala Ala Leu Ala Gln Val Asp Thr
            355                 360                 365

Leu Arg Ser Asp Leu Ala Ala Val Gln Asn Arg Phe Asn Ser Ala Ile
370                 375                 380

Thr Asn Leu Gly Asn Thr Val Asn Asn Leu Thr Ser Ala Arg
385                 390                 395

<210> SEQ ID NO 22
<211> LENGTH: 290
<212> TYPE: PRT
<213> ORGANISM: Artificial
<220> FEATURE:
<223> OTHER INFORMATION: Synthetic

<400> SEQUENCE: 22

Met Ala Leu Thr Val Asn Thr Asn Ile Ala Ser Leu Asn Thr Gln Arg
1               5                   10                  15

Asn Leu Asn Asn Ser Ser Ala Ser Leu Asn Thr Ser Leu Gln Arg Leu
            20                  25                  30

Ser Thr Gly Ser Arg Ile Asn Ser Ala Lys Asp Asp Ala Ala Gly Leu
        35                  40                  45

Gln Ile Ala Asn Arg Leu Thr Ser Gln Val Asn Gly Leu Asn Val Ala
    50                  55                  60

Thr Lys Asn Ala Asn Asp Gly Ile Ser Leu Ala Gln Thr Ala Glu Gly
65                  70                  75                  80

Ala Leu Gln Gln Ser Thr Asn Ile Leu Gln Arg Met Arg Asp Leu Ser
                85                  90                  95

Leu Gln Ser Ala Asn Gly Ser Asn Ser Asp Ser Glu Arg Thr Ala Leu
            100                 105                 110

Asn Gly Glu Val Lys Gln Leu Gln Lys Glu Leu Asp Arg Ile Ser Asn
        115                 120                 125

Thr Thr Thr Phe Gly Gly Arg Lys Leu Leu Asp Gly Ser Phe Gly Val
    130                 135                 140

Ala Ser Phe Gln Val Gly Ser Ala Ala Asn Glu Ile Ile Ser Val Gly
145                 150                 155                 160

Ile Gly Gly Gly Lys Leu Met Ile Lys Leu Lys Phe Gly Val Phe Phe
                165                 170                 175

Thr Val Leu Leu Ser Ser Ala Tyr Ala His Gly Thr Pro Gln Asn Ile
            180                 185                 190

Thr Asp Leu Cys Ala Glu Tyr His Asn Thr Gln Ile His Thr Leu Asn
        195                 200                 205

Asp Lys Ile Phe Ser Tyr Thr Glu Ser Leu Ala Gly Lys Arg Glu Met
    210                 215                 220

Ala Ile Ile Thr Phe Lys Asn Gly Ala Thr Phe Gln Val Glu Val Pro
225                 230                 235                 240

```
Gly Ser Gln His Ile Asp Ser Gln Lys Lys Ala Ile Glu Arg Met Lys
            245                 250                 255

Asp Thr Leu Arg Ile Ala Tyr Leu Thr Glu Ala Lys Val Glu Lys Leu
        260                 265                 270

Cys Val Trp Asn Asn Lys Thr Pro His Ala Ile Ala Ala Ile Ser Met
    275                 280                 285

Ala Asn
    290

<210> SEQ ID NO 23
<211> LENGTH: 39
<212> TYPE: PRT
<213> ORGANISM: Artificial
<220> FEATURE:
<223> OTHER INFORMATION: Synthetic

<400> SEQUENCE: 23

Gly Ala Leu Asn Glu Ile Asn Asn Asn Leu Gln Arg Val Arg Glu Leu
1               5                   10                  15

Ala Val Gln Ser Ala Asn Ser Thr Asn Ser Gln Ser Asp Leu Asp Ser
            20                  25                  30

Ile Gln Ala Glu Ile Thr Gln
        35

<210> SEQ ID NO 24
<211> LENGTH: 44
<212> TYPE: PRT
<213> ORGANISM: Artificial
<220> FEATURE:
<223> OTHER INFORMATION: Synthetic

<400> SEQUENCE: 24

Thr Gln Phe Ser Gly Val Lys Val Leu Ala Gln Asp Asn Thr Leu Thr
1               5                   10                  15

Ile Gln Val Gly Ala Asn Asp Gly Glu Thr Ile Asp Ile Asp Leu Lys
            20                  25                  30

Gln Ile Asn Ser Gln Thr Leu Gly Leu Asp Thr Leu
        35                  40

<210> SEQ ID NO 25
<211> LENGTH: 50
<212> TYPE: PRT
<213> ORGANISM: Artificial
<220> FEATURE:
<223> OTHER INFORMATION: Synthetic

<400> SEQUENCE: 25

Glu Gly Ala Leu Asn Glu Ile Asn Asn Asn Leu Gln Arg Val Arg Glu
1               5                   10                  15

Leu Ala Val Gln Ser Ala Asn Ser Thr Asn Ser Gln Ser Asp Leu Asp
            20                  25                  30

Ser Ile Gln Ala Glu Ile Thr Gln Arg Leu Asn Glu Ile Asp Arg Val
        35                  40                  45

Asn Gly
    50

<210> SEQ ID NO 26
<211> LENGTH: 82
<212> TYPE: PRT
<213> ORGANISM: Artificial
<220> FEATURE:
<223> OTHER INFORMATION: Synthetic
```

-continued

<400> SEQUENCE: 26

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Phe Thr Ala Asn Ile Lys Gly Leu Thr Gln Ala Ser
    50                  55                  60

Arg Asn Ala Asn Asp Gly Ile Ser Ile Ala Gln Thr Thr Glu Gly Ala
65                  70                  75                  80

Leu Asn

<210> SEQ ID NO 27
<211> LENGTH: 32
<212> TYPE: PRT
<213> ORGANISM: Artificial
<220> FEATURE:
<223> OTHER INFORMATION: Synthetic

<400> SEQUENCE: 27

Leu Gln Lys Ile Asp Ala Ala Leu Ala Gln Val Asp Thr Leu Arg Ser
1               5                   10                  15

Asp Leu Gly Ala Val Gln Asn Arg Phe Asn Ser Ala Ile Thr Asn Leu
            20                  25                  30

<210> SEQ ID NO 28
<211> LENGTH: 29
<212> TYPE: PRT
<213> ORGANISM: Artificial
<220> FEATURE:
<223> OTHER INFORMATION: Synthetic

<400> SEQUENCE: 28

Thr Leu Arg Ser Asp Leu Gly Ala Val Gln Asn Arg Phe Asn Ser Ala
1               5                   10                  15

Ile Thr Asn Leu Gly Asn Thr Val Asn Asn Leu Ser Ser
            20                  25

<210> SEQ ID NO 29
<211> LENGTH: 51
<212> TYPE: PRT
<213> ORGANISM: Artificial
<220> FEATURE:
<223> OTHER INFORMATION: Synthetic

<400> SEQUENCE: 29

Glu Gln Ala Ala Lys Thr Thr Glu Asn Pro Leu Gln Lys Ile Asp Ala
1               5                   10                  15

Ala Leu Ala Gln Val Asp Thr Leu Arg Ser Asp Leu Gly Ala Val Gln
            20                  25                  30

Asn Arg Phe Asn Ser Ala Ile Thr Asn Leu Gly Asn Thr Val Asn Asn
        35                  40                  45

Leu Ser Ser
    50

<210> SEQ ID NO 30
<211> LENGTH: 328
<212> TYPE: PRT
<213> ORGANISM: Artificial

<220> FEATURE:
<223> OTHER INFORMATION: Synthetic

<400> SEQUENCE: 30

Met Arg Gly Ser His His His His His His Gly Met Ala Ser Met Thr
1               5                   10                  15

Gly Gln Gln Met Gly Arg Asp Leu Tyr Asp Asp Asp Lys Asp Pro
            20                  25                  30

Met Ala Gln Val Ile Asn Thr Asn Ser Leu Ser Leu Leu Thr Gln Asn
            35                  40                  45

Asn Leu Asn Lys Ser Gln Ser Ser Leu Ser Ser Ala Ile Glu Arg Leu
        50                  55                  60

Ser Ser Gly Leu Arg Ile Asn Ser Ala Lys Asp Asp Ala Ala Gly Gln
65                  70                  75                  80

Ala Ile Ala Asn Arg Phe Thr Ser Asn Ile Lys Gly Leu Thr Gln Ala
                85                  90                  95

Ser Arg Asn Ala Asn Asp Gly Ile Ser Ile Ala Gln Thr Thr Glu Gly
            100                 105                 110

Ala Leu Asn Glu Ile Asn Asn Asn Leu Gln Arg Val Arg Glu Leu Ser
        115                 120                 125

Val Gln Ala Thr Asn Gly Thr Asn Ser Asp Ser Asp Leu Lys Ser Ile
130                 135                 140

Gln Asp Glu Ile Gln Gln Arg Leu Glu Glu Ile Asp Arg Val Ser Asn
145                 150                 155                 160

Gln Thr Gln Phe Asn Gly Val Lys Val Leu Ser Gln Asp Asn Gln Met
                165                 170                 175

Lys Ile Gln Val Gly Ala Asn Asp Gly Glu Thr Ile Thr Ile Asp Leu
            180                 185                 190

Gln Lys Ile Asp Val Lys Ser Leu Gly Leu Asp Gly Phe Asn Val Asn
        195                 200                 205

Ser Pro Gly Ile Ser Gly Gly Gly Ile Leu Asp Ser Met Gly
210                 215                 220

Thr Leu Ile Asn Glu Asp Ala Ala Ala Lys Lys Ser Thr Ala Asn
225                 230                 235                 240

Pro Leu Ala Ser Ile Asp Ser Ala Leu Ser Lys Val Asp Ala Val Arg
                245                 250                 255

Ser Ser Leu Gly Ala Ile Gln Asn Arg Phe Asp Ser Ala Ile Thr Asn
            260                 265                 270

Leu Gly Asn Thr Val Thr Asn Leu Asn Ser Ala Arg Ser Arg Ile Glu
        275                 280                 285

Asp Ala Asp Tyr Ala Thr Glu Val Ser Asn Met Ser Lys Ala Gln Ile
290                 295                 300

Leu Gln Gln Ala Gly Thr Ser Val Leu Ala Gln Ala Asn Gln Val Pro
305                 310                 315                 320

Gln Asn Val Leu Ser Leu Leu Arg
                325

<210> SEQ ID NO 31
<211> LENGTH: 23
<212> TYPE: PRT
<213> ORGANISM: Artificial
<220> FEATURE:
<223> OTHER INFORMATION: Synthetic

<400> SEQUENCE: 31

Phe Leu Gly Ile Ala Glu Ala Ile Asp Ile Gly Asn Gly Trp Glu Gly

```
1               5              10              15
Met Glu Phe Gly Gly Gly Cys
            20

<210> SEQ ID NO 32
<211> LENGTH: 6
<212> TYPE: PRT
<213> ORGANISM: Artificial
<220> FEATURE:
<223> OTHER INFORMATION: Synthetic

<400> SEQUENCE: 32

Gly Gly Gly Gly Gly Gly
1               5

<210> SEQ ID NO 33
<211> LENGTH: 5
<212> TYPE: PRT
<213> ORGANISM: Artificial
<220> FEATURE:
<223> OTHER INFORMATION: Synthetic

<400> SEQUENCE: 33

Gly Gly Gly Gly Thr
1               5

<210> SEQ ID NO 34
<211> LENGTH: 6
<212> TYPE: PRT
<213> ORGANISM: Artificial
<220> FEATURE:
<223> OTHER INFORMATION: Synthetic

<400> SEQUENCE: 34

Gly Gly Gly Pro Pro Pro
1               5

<210> SEQ ID NO 35
<211> LENGTH: 7
<212> TYPE: PRT
<213> ORGANISM: Artificial
<220> FEATURE:
<223> OTHER INFORMATION: Synthetic

<400> SEQUENCE: 35

Gly Gly Gly Ala Pro Pro Pro
1               5
```